US012232415B2

United States Patent
Kamtekar

(10) Patent No.: US 12,232,415 B2
(45) Date of Patent: Feb. 18, 2025

(54) MOLECULAR MATERIALS BASED ON PHENOXYAZINE CORE FOR HETEROJUNCTION ORGANIC SOLAR CELLS

(71) Applicant: Sumitomo Chemical Co., Ltd., Tokyo (JP)

(72) Inventor: Kiran Kamtekar, Cambridgeshire (GB)

(73) Assignee: Sumitomo Chemical Co., Ltd., Tokyo (JP)

( * ) Notice: Subject to any disclaimer, the term of this patent is extended or adjusted under 35 U.S.C. 154(b) by 34 days.

(21) Appl. No.: 17/771,454

(22) PCT Filed: Oct. 23, 2020

(86) PCT No.: PCT/GB2020/052685
§ 371 (c)(1),
(2) Date: Apr. 22, 2022

(87) PCT Pub. No.: WO2021/079140
PCT Pub. Date: Apr. 29, 2021

(65) Prior Publication Data
US 2022/0407015 A1    Dec. 22, 2022

(30) Foreign Application Priority Data

Oct. 24, 2019  (EP) .................................... 19205205
Jul. 29, 2020  (GB) .................................... 2011800

(51) Int. Cl.
H10K 30/30       (2023.01)
C07D 495/14      (2006.01)
H10K 85/60       (2023.01)

(52) U.S. Cl.
CPC ......... H10K 85/657 (2023.02); C07D 495/14 (2013.01); H10K 85/626 (2023.02); H10K 85/655 (2023.02); H10K 30/30 (2023.02)

(58) Field of Classification Search
CPC ...... H01L 31/00–078; H10K 30/00–89; Y02E 10/50–60
(Continued)

(56) References Cited

U.S. PATENT DOCUMENTS

2016/0272656 A1 *  9/2016  Cho .................. C07D 495/04
2017/0054077 A1 *  2/2017  Bender ............... H10K 30/30
(Continued)

FOREIGN PATENT DOCUMENTS

EP     3064500 A2      9/2016
KR     20150114418 A  10/2015
KR     20180104398 A  * 9/2018

OTHER PUBLICATIONS

KR-20180104398-A English (Year: 2018).*
(Continued)

*Primary Examiner* — Bach T Dinh
(74) *Attorney, Agent, or Firm* — Wolf, Greenfield & Sacks, P.C.

(57) ABSTRACT

A composition comprising an electron acceptor material and an electron donor material wherein the electron acceptor material is a compound of formula (I): EAG-EDG-EAG (I) wherein each EAG is an electron-accepting group and EDG is a group of formula (II): (II) wherein: n is at least 1; each m is independently 0 or at least 1; each X, Y and A is independently O, S or Se; Z, independently in each occurrence if n is greater than 1, is O, S, C=O or NR$^9$ wherein R$^9$ is H or a substituent; and R$^1$-R$^8$ are each independently selected from H or a substituent. The composition may be used as photosensitive organic layer of an organic photodetector.

(Continued)

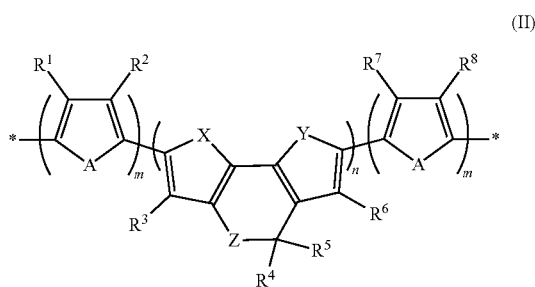

(II)

16 Claims, 2 Drawing Sheets

(58) Field of Classification Search
USPC .................................................. 136/243–265
See application file for complete search history.

(56) References Cited

U.S. PATENT DOCUMENTS

2017/0062139 A1* 3/2017 Gong ..................... H10K 30/00
2019/0284210 A1* 9/2019 Kim ..................... C07D 495/04

OTHER PUBLICATIONS

Extended European Search Report dated Feb. 20, 2020 in connection with European Application No. 19205205.8.
International Search Report and Written Opinion mailed Jan. 26, 2021 in connection with International Application No. PCT/GB2020/052685.
Jung et al., A small molecule composed of dithienopyran and diketopyrrolopyrrole as versatile electron donor compatible with both fullerene and nonfullerene electron acceptors for high performance organic solar cells. Chemistry of Materials. Jun. 2015;27(13):4865-70.
Bukovsky et al., Structures and structure-related electronic properties of new C60(CF3)10 isomers. Journal of Fluorine Chemistry, vol. 185, May 2016, pp. 103-117.
Lucia Pinto et al., Catechol versus carboxyl linkage impact on DSSC performance of synthetic pyranoflavylium salts. Dyes and Pigments. Nov. 2019;170(107577).
Hudhomme, An Overview of Molecular acceptors for organic solar cells. EPJ Photovolt. Jul. 8, 2013;4(4). 11 Pages.
No Author Listed, PCBM. Safety Data Sheet. Ossila. Nov. 14, 2022. Revision #2. 5 Pages.

* cited by examiner

MOLECULAR MATERIALS BASED ON PHENOXYAZINE CORE FOR HETEROJUNCTION ORGANIC SOLAR CELLS

RELATED APPLICATIONS

This application is a national stage filing under 35 U.S.C. § 371 of International PCT Application PCT/GB2020/052685, filed Oct. 23, 2020, which claims priority to United Kingdom patent application, GB 2011800.6 filed on Jul. 29, 2020, and to European patent application, EP 19205205.8, filed on Oct. 24, 2019, each of which is incorporated herein by reference.

BACKGROUND

Embodiments of the present disclosure relate to materials suitable for use in organic photoresponsive devices, and devices containing said materials.

Organic photovoltaic devices and organic photodetectors (OPDs) are known.

EP 3064500 discloses certain molecules having Chemical Formula 1 as an end unit and their use in solar cells:

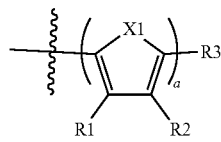

[Chemical Formula 1]

wherein X1 is CRR', NR, O, SiRR', PR, S, GeRR' Se or Te.

Jung et al, "A Small Molecule Composed of Dithienopyran and Diketopyrrolopyrrole as Versatile Electron Donor Compatible with Both Fullerene and Nonfullerene Electron Acceptors for High Performance Organic Solar Cells", Chem. Mater. 2015, 27, 13, 4865-4870 discloses a compound DTP-DPP composed of dithieonpyran and diketopyrrolopyrrole.

Chu et al, "Dithieno[3,2-b:2',3'-d]pyran-containing organic D-π-A sensitizers for dye-sensitized solar cells", discloses D-π-A sensitisers incorporating a dithieno[3,2-b:2',3'-d]pyran and dye-sensitised solar cells containing these sensitisers.

SUMMARY

A summary of aspects of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects and/or a combination of aspects that may not be set forth.

According to some embodiments, the present disclosure provides a composition containing an electron acceptor material and an electron donor material.

The electron acceptor material is a compound of formula (I):

EAG-EDG-EAG     (I)

wherein each EAG is an electron-accepting group and EDG is a group of formula (II):

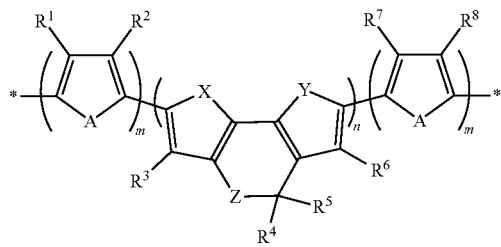

wherein:
n is at least 1;
each m is independently 0 or at least 1;
each X, Y and A is independently O, S or Se;
Z, independently in each occurrence if n is greater than 1, is O, S, C=O or $NR^9$ wherein $R^9$ is H or a substituent;
$R^1$-$R^8$ are each independently selected from H or a substituent.

Optionally, each EAG is a group of formula (V):

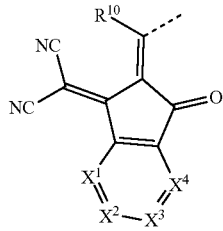

wherein:
$R^{10}$ in each occurrence is H or a substituent selected from the group consisting of: $C_{1-12}$ alkyl wherein one or more non-adjacent, non-terminal C atoms may be replaced with O, S, COO or CO and one or more H atoms of the alkyl may be replaced with F; and an aromatic group $Ar^2$ which is unsubstituted or substituted with one or more substituents selected from F and $C_{1-12}$ alkyl wherein one or more non-adjacent, non-terminal C atoms may be replaced with O, S, COO or CO;
 represents a linking position to * of EDG; and
each $X^1$-$X^4$ is independently $CR^{12}$ or N wherein $R^{12}$ in each occurrence is H or a substituent selected from $C_{1-20}$ hydrocarbyl and an electron withdrawing group.

Optionally, at least one $R^{12}$ is an electron-withdrawing group selected from F, Br, Cl and CN.

Optionally, each m is 0 or 1.
Optionally, X and Y are each S.
Optionally, Z is O or $NR^9$.
Optionally, at least one m is at least 1 and the or each A is S.

Optionally, $R^1$-$R^8$ are each independent selected from the group consisting of: H;
linear, branched or cyclic $C_{1-20}$ alkyl wherein one or more non-adjacent, non-terminal C atoms may be replaced by O, S, $NR^{12}$, CO or COO and wherein one or more H atoms of the $C_{1-20}$ alkyl may be replaced with F; and
a group of formula -(Ak)u-$(Ar^1)$v wherein Ak is a $C_{1-12}$ alkylene chain in which one or more C atoms may be replaced with O, S, CO or COO; u is 0 or 1; $Ar^1$ in each occurrence is independently an aromatic or heteroaromatic group which is unsubstituted or substituted with one or more substituents; and v is at least 1.

Optionally, each * is bound directly to an acyclic carbon-carbon double bond of EAG.

According to some embodiments, the present disclosure provides an organic photoresponsive device including an anode; a cathode; and a photosensitive organic layer disposed between the anode and cathode. The photosensitive organic layer comprises a composition as described herein.

Optionally, the photoresponsive device is an organic photodetector.

According to some embodiments, the present disclosure provides a method of forming an organic photoresponsive device as described herein in which the photosensitive organic layer is formed over one of the anode and cathode and the other of the anode and cathode is formed over the photosensitive organic layer.

Optionally, formation of the photosensitive organic layer comprises deposition of a formulation comprising composition dissolved or dispersed in one or more solvents.

According to some embodiments, the present disclosure provides a sensor having a light source and an organic photoresponsive device as described herein configured to detect light emitted from the light source.

Optionally, the light source emits light having a peak wavelength greater than 750 nm.

Optionally, the organic photodetector is configured to detect light emitted from the light source following one or more of absorption, reflection and downconversion of light emitted from the light source.

According to some embodiments, there is provided a method of determining the presence and/or concentration of a target substance in a sample, the method comprising illuminating the sample and measuring a response of an organic photodetector as described herein. The organic photodetector may be part of a sensor as described herein.

DESCRIPTION OF DRAWINGS

The disclosed technology and accompanying figures describe some implementations of the disclosed technology.

Figure 1:
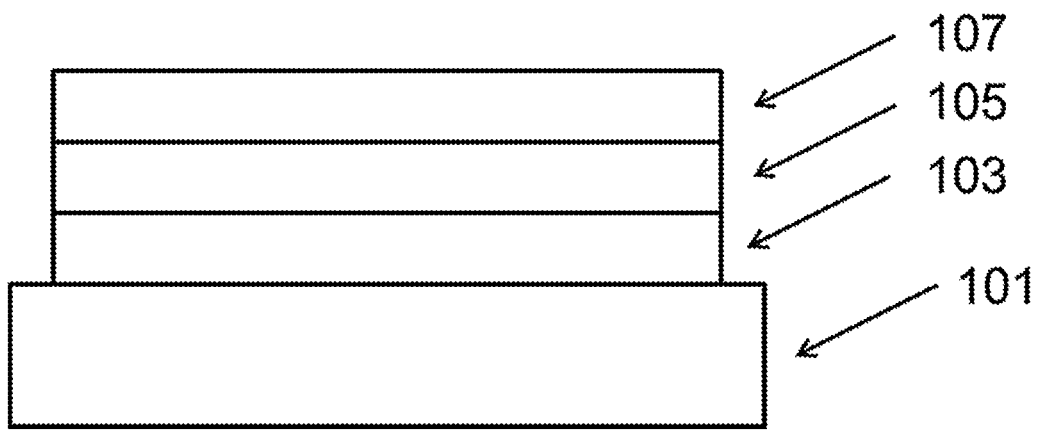
FIG. 1 illustrates an organic photoresponsive device according to some embodiments.

The drawings are not drawn to scale and have various viewpoints and perspectives. The drawings are some implementations and examples. Additionally, some components and/or operations may be separated into different blocks or combined into a single block for the purposes of discussion of some of the embodiments of the disclosed technology. Moreover, while the technology is amenable to various modifications and alternative forms, specific embodiments have been shown by way of example in the drawings and are described in detail below. The intention, however, is not to limit the technology to the particular implementations described. On the contrary, the technology is intended to cover all modifications, equivalents, and alternatives falling within the scope of the technology as defined by the appended claims.

DETAILED DESCRIPTION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." Additionally, the words "herein," "above," "below," and words of similar import, when used in this application, refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list. References to a layer "over" another layer when used in this application means that the layers may be in direct contact or one or more intervening layers are may be present. References to a layer "on" another layer when used in this application means that the layers are in direct contact. References to a specific atom include any isotope of that atom unless specifically stated otherwise.

The teachings of the technology provided herein can be applied to other systems, not necessarily the system described below. The elements and acts of the various examples described below can be combined to provide further implementations of the technology. Some alternative implementations of the technology may include not only additional elements to those implementations noted below, but also may include fewer elements.

These and other changes can be made to the technology in light of the following detailed description. While the description describes certain examples of the technology, and describes the best mode contemplated, no matter how detailed the description appears, the technology can be practiced in many ways. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms.

In the following description, for the purposes of explanation, numerous specific details are set forth in order to provide a thorough understanding of implementations of the disclosed technology. It will be apparent, however, to one skilled in the art that embodiments of the disclosed technology may be practiced without some of these specific details.

The present inventors have found that compounds of formula (I) may be used as an acceptor in a donor-acceptor system used in an organic photoresponsive device, e.g. a photovoltaic device such as a solar cell or an organic photodetector.

n of formula (I) may be selected according to a desired wavelength of light to be absorbed. Absorption of light in the visible region (e.g. about 400-750 nm) is preferred where n is 1.

The compounds may absorb long wavelengths of light, e.g. greater than about 750 nm, particularly where n is at least 2, making them suitable for use in organic photodetectors for detection of light in the near-infrared range.

FIG. 1 illustrates an organic photoresponsive device according to some embodiments of the present disclosure. The organic photoresponsive device comprises a cathode 103, an anode 107 and a bulk heterojunction layer 105 disposed between the anode and the cathode. The organic photoresponsive device may be supported on a substrate 101, optionally a glass or plastic substrate.

FIG. 1 illustrates an arrangement in which the cathode is disposed between the substrate and the anode. In other embodiments, the anode may be disposed between the cathode and the substrate.

The bulk heterojunction layer comprises a mixture of one or more electron acceptors including at least one electron acceptor of formula (I) and at least one electron donor. Optionally, the bulk heterojunction layer consists of the one or more electron acceptors and the one or more electron donors.

In some embodiments, the bulk heterojunction layer comprises an electron acceptor of formula (I) and one or more further electron acceptors. Further electron acceptors may be selected from fullerene acceptors and non-fullerene acceptors. Non-fullerene acceptors are described in, for example, Cheng et al, "Next-generation organic photovoltaics based on non-fullerene acceptors", Nature Photonics volume 12, pages 131-142 (2018), the contents of which are incorporated herein by reference, and which include, without limitation, PDI, ITIC, ITIC, IEICO and derivatives thereof, e.g. fluorinated derivatives thereof such as ITIC-4F and IEICO-4F. Exemplary fullerene electron acceptor materials are $C_{60}$, $C_{70}$, $C_{76}$, $C_{78}$ and $C_{84}$ fullerenes or a derivative thereof including, without limitation, PCBM-type fullerene derivatives (including phenyl-C61-butyric acid methyl ester ($C_{60}$PCBM), TCBM-type fullerene derivatives (e.g. tolyl-C61-butyric acid methyl ester ($C_{60}$TCBM)), and ThCBM-type fullerene derivatives (e.g. thienyl-C61-butyric acid methyl ester ($C_{60}$ThCBM).

In some embodiments, the bulk heterojunction layer consists of a single electron acceptor and a single electron donor. Each of the anode and cathode may independently be a single conductive layer or may comprise a plurality of layers.

The organic photoresponsive device may comprise layers other than the anode, cathode and bulk heterojunction layer shown in FIG. 1. In some embodiments, a hole-transporting layer is disposed between the anode and the bulk heterojunction layer. In some embodiments, an electron-transporting layer is disposed between the cathode and the bulk heterojunction layer. In some embodiments, a work function modification layer is disposed between the bulk heterojunction layer and the anode, and/or between the bulk heterojunction layer and the cathode.

In the case where the organic photoresponsive device is an organic photodetector (OPD), it may be provided in a circuit connected to a voltage source for applying a reverse bias to the device and/or a device configured to measure photocurrent. The voltage applied to the photodetector may be variable. In some embodiments, the photodetector may be continuously biased when in use.

In some embodiments, a photodetector system comprises a plurality of photodetectors as described herein, such as an image sensor of a camera.

In some embodiments, a sensor may comprise an OPD as described herein and a light source wherein the OPD is configured to receive light emitted from the light source.

In some embodiments, the light from the light source may or may not be changed before reaching the OPD. For example, the light may be reflected, filtered, down-converted or up-converted before it reaches the OPD.

The bulk heterojunction layer may contain an electron acceptor (n-type) compound of formula (I):

EAG-EDG-EAG  (I)

in which EAG is an electron-accepting group and EDG is an electron donating group of formula (II):

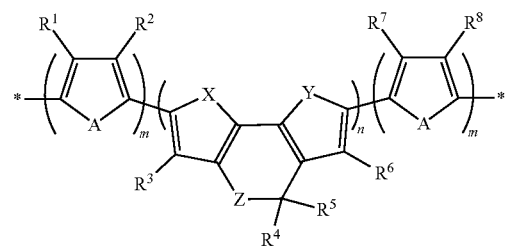

wherein:
n is at least 1;
each m is independently 0 or at least 1;
each X, Y and A is independently O, S or Se;
Z, independently in each occurrence if n is greater than 1, is O, S or $NR^9$ wherein $R^9$ is H or a substituent; and
$R^1$ and $R^8$ are each independently H or a substituent.
n is preferably 1, 2 or 3.

In the case where n is greater than 1, the n groups may be linked in any orientation. For example, in the case where n=2, the group of formula (II) may be any of:

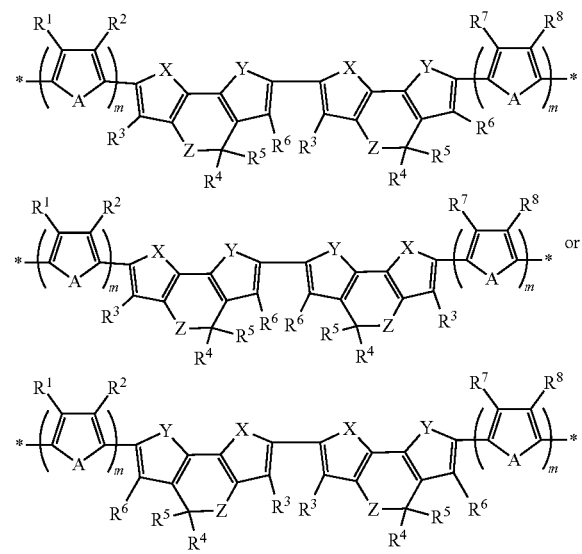

In the case where n is greater than 1, X, Y, Z and $R^3$-$R^6$ independently in each occurrence may be the same or different.

EAG has a LUMO level that is deeper (i.e. further from vacuum) than EDG, preferably at least 1 eV deeper. The LUMO levels of EAG and EDG may be as determined by modelling the LUMO levels of EAG-H and H-EDG-H, i.e. by replacing the bonds between EAG and EDG with bonds to a hydrogen atom. Modelling may be performed using Gaussian09 software available from Gaussian using Gaussian09 with B3LYP (functional) and LACVP* (Basis set).

Each m is preferably 0 or 1. Each m is preferably the same.

X and Y are each preferably S.

Z is preferably O or $NR^9$. A compound of formula (I) in which Z is $NR^9$ may have an absorption peak at a longer wavelength than a compound in which Z is O.

Optionally, $R^9$ is a $C_{1-20}$ hydrocarbyl, e.g. a $C_{1-20}$ alkyl or a $C_{6-14}$ aromatic group, e.g. phenyl, which is unsubstituted or substituted with one or more $C_{1-12}$ alkyl groups.

Each A, where present, is preferably S.

Optionally, $R^1$, $R^2$, $R^4$, $R^5$, $R^7$ and $R^8$ are each independent selected from the group consisting of:

H;

linear, branched or cyclic $C_{1-20}$ alkyl wherein one or more non-adjacent, non-terminal C atoms may be replaced by O, S, $NR^{12}$, CO or COO and wherein one or more H atoms of the $C_{1-20}$ alkyl may be replaced with F; and a group of formula -(Ak)u-$(Ar^1)$v wherein Ak is a $C_{1-12}$ alkylene chain in which one or more C atoms may be replaced with O, S, CO or COO; u is 0 or 1; $Ar^1$ in each occurrence is independently an aromatic or heteroaromatic group which is unsubstituted or substituted with one or more substituents; and v is at least 1, optionally 1, 2 or 3.

By "non-terminal" C atom of an alkyl group as used herein is meant a C atom of the alkyl other than the methyl C atom of a linear (n-alkyl) chain or the methyl C atoms of a branched alkyl chain.

$Ar^1$ is preferably phenyl.

Where present, substituents of $Ar^1$ may be a substituent $R^{11}$ which in each occurrence is independently selected from $C_{1-20}$ alkyl wherein one or more non-adjacent, non-terminal C atoms may be replaced by O, S, $NR^9$, CO or COO and one or more H atoms of the $C_{1-20}$ alkyl may be replaced with F.

$R^3$ and $R^6$ may each independently be selected from: groups described above with respect to $R^1$, $R^2$, $R^4$, $R^5$, $R^7$ and $R^8$; and a group of formula $—B(R^{14})_2$ wherein $R^{14}$ in each occurrence is a substituent, optionally a $C_{1-20}$ hydrocarbyl group. In the case where m=0, the B atom of $—B(R^{14})_2$ may form a dative bond with an aromatic N atom of an adjacent electron-accepting group.

Preferably, $R^1$ and $R^8$ (where present) are each H.

Preferably, $R^2$ and $R^7$ (where present) are each a substituent, preferably $C_{1-20}$ alkyl or $C_{1-20}$ alkoxy.

Preferably, $R^3$ is H.

Preferably, $R^6$ is H.

Preferably, $R^4$ and $R^5$ are each a substituent, more preferably a substituent selected from $C_{1-20}$ alkyl; unsubstituted phenyl; and phenyl substituted with one or more substituents, optionally one or more $C_{1-12}$ alkyl or $C_{1-12}$ alkoxy groups.

Optionally, each * is bound directly to an acyclic carbon-carbon double bond of EAG.

By "acyclic carbon-carbon double bond" as used herein is meant a carbon-carbon double bond in which the two carbon atoms of the double bond are not ring atoms of the same ring. In some preferred embodiments, one of the carbon atoms of the double bond is a ring carbon atom and the other carbon atom is not a ring carbon atom.

The EAGs may be the same or different, preferably the same.

Optionally, each EAG is selected from formulae (III)-(XV):

(III)

(IVa)

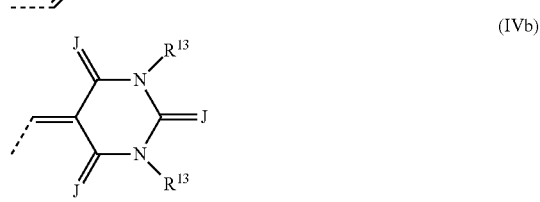
(IVb)

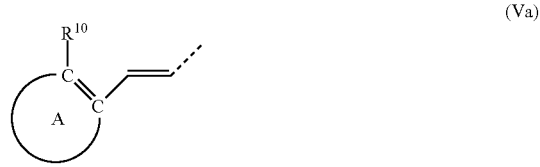
(Va)

(Vb)

(VIa)

(VIb)

(VIc)

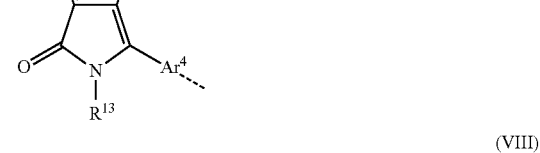
(VII)

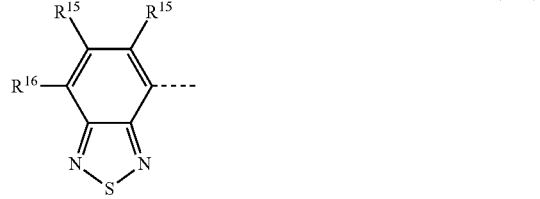
(VIII)

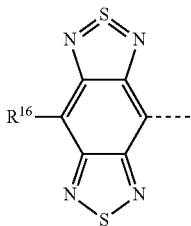
(IX)

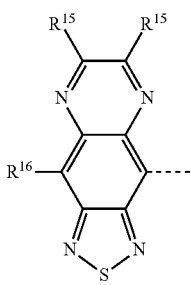
(X)

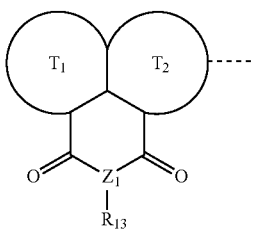
(XI)

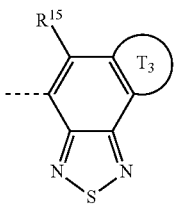
(XII)

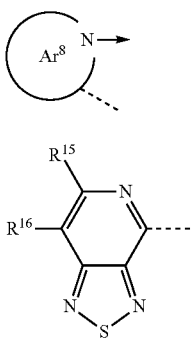
(XIV)

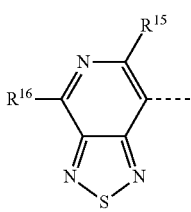
(XV)

A is a 5- or 6-membered ring which is unsubstituted or substituted with one or more substituents and which may be fused to one or more further rings.

$R^{10}$ is H or a substituent, preferably a substituent selected from the group consisting of $C_{1-12}$ alkyl wherein one or more non-adjacent, non-terminal C atoms may be replaced with O, S, COO or CO and one or more H atoms of the alkyl may be replaced with F; and an aromatic group $Ar^2$, optionally phenyl, which is unsubstituted or substituted with one or more substituents selected from F and $C_{1-12}$ alkyl wherein one or more non-adjacent, non-terminal C atoms may be replaced with O, S, COO or CO.

Preferably, $R^{10}$ is H.

J is O or S.

$R^{13}$ in each occurrence is a substituent, optionally $C_{1-12}$ alkyl wherein one or more non-adjacent, non-terminal C atoms may be replaced with O, S, COO or CO and one or more H atoms of the alkyl may be replaced with F.

$R^{15}$ in each occurrence is independently H; F; $C_{1-12}$ alkyl wherein one or more non-adjacent, non-terminal C atoms may be replaced with O, S, COO or CO and one or more H atoms of the alkyl may be replaced with F; or an aromatic group $Ar^2$, optionally phenyl, which is unsubstituted or substituted with one or more substituents selected from F and $C_{1-12}$ alkyl wherein one or more non-adjacent, non-terminal C atoms may be replaced with O, S, COO or CO.

$R^{16}$ is a substituent, preferably a substituent selected from:

—$(Ar^3)_w$ wherein $Ar^3$ in each occurrence is independently an unsubstituted or substituted aryl or heteroaryl group, preferably thiophene, and w is 1, 2 or 3;

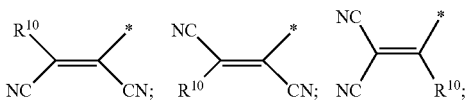
(XIII)

and $C_{1-12}$ alkyl wherein one or more non-adjacent, non-terminal C atoms may be replaced with O, S, COO or CO and one or more H atoms of the alkyl may be replaced with F.

$Ar^4$ is a 5-membered heteroaromatic group, preferably thiophene or furan, which is unsubstituted or substituted with one or more substituents.

Substituents of $Ar^3$ and $Ar^4$, where present, are optionally selected from $C_{1-12}$ alkyl wherein one or more non-adjacent, non-terminal C atoms may be replaced with O, S, COO or CO and one or more H atoms of the alkyl may be replaced with F.

$Z^1$ is N or P $T^1$, $T^2$ and $T^3$ each independently represent an aryl or a heteroaryl ring which may be fused to one or more further rings. Substituents of $T^1$, $T^2$ and $T^3$, where present, are optionally selected from non-H groups of $R^{15}$.

$Ar^8$ is a fused heteroaromatic group which is unsubstituted or substituted with one or more non-H substituents $R^{10}$.

A preferred group of formula (III) is formula (IIIa).

Preferably at least one, more preferably each, EAG is a group of formula (IIIa):

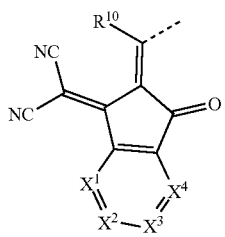

(IIIa)

wherein:
R$^{10}$ is as described above;
---- represents a linking position to * of EDG; and
each X$^1$-X$^4$ is independently CR$^{12}$ or N wherein R$^{12}$ in each occurrence is H or a substituent selected from C$_{1-20}$ hydrocarbyl and an electron withdrawing group. Optionally, the electron withdrawing group is F, Cl, Br or CN.

The C$_{1-20}$ hydrocarbyl group R$^{12}$ may be selected from C$_{1-20}$ alkyl; unsubstituted phenyl; and phenyl substituted with one or more C$_{1-12}$ alkyl groups.

Exemplary compounds of formula (Va) or (Vb) include:

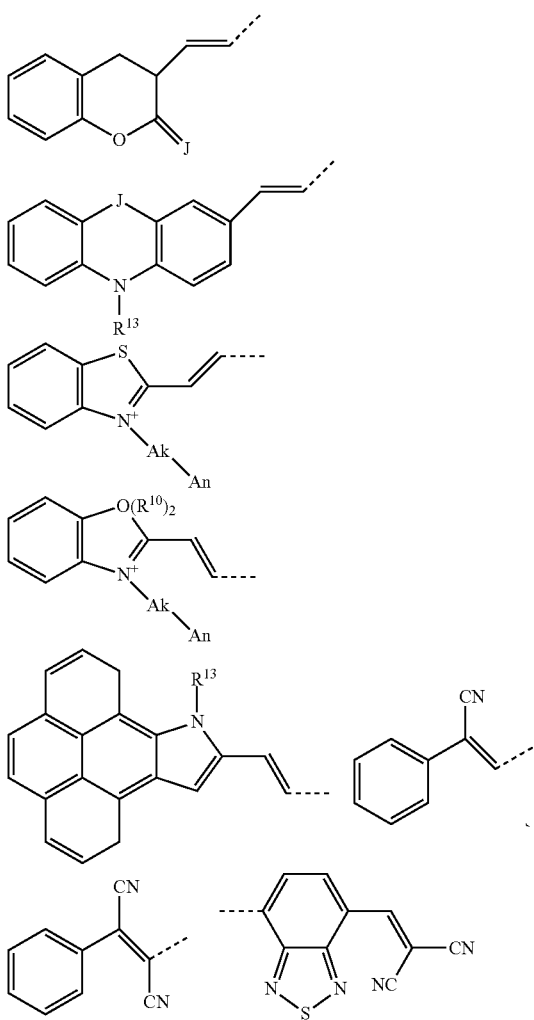

wherein Ak is a C$_{1-12}$ alkylene chain in which one or more C atoms may be replaced with O, S, CO or COO; An is an anion, optionally —SO$_3^-$; and each benzene ring is independently unsubstituted or substituted with one or more substituents selected from substituents described with reference to R$^{10}$.

Exemplary EAGs of formula (XI) are:

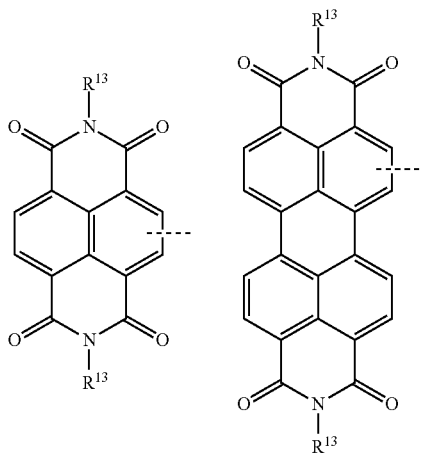

An exemplary EAG group of formula (XII) is:

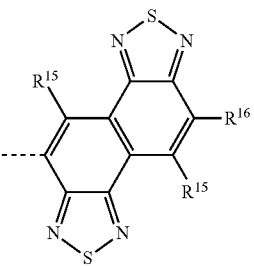

In the case where at least one EAG is a group of formula (XIII), at least one m is 0; at least one of R$^3$ and R$^6$ is —B(R$^{14}$)$_2$ wherein R$^{14}$ in each occurrence is a substituent, optionally a C$_{1-20}$ hydrocarbyl group; → is a bond to the boron atom —B(R$^{14}$)$_2$ of R$^3$ or R$^6$; and --- is the bond to EDG.

Optionally, R$^{14}$ is selected from C$_{1-12}$ alkyl; unsubstituted phenyl; and phenyl substituted with one or more C$_{1-12}$ alkyl groups.

EDG, EAG and the B(R$^{14}$)$_2$ substituent R$^3$ or R$^6$ of EDG may be linked together to form a 5- or 6-membered ring.

In some embodiments, EAG of formula (XIII) is selected from formulae (XIIIa), (XIIIb) and (XIIIc):

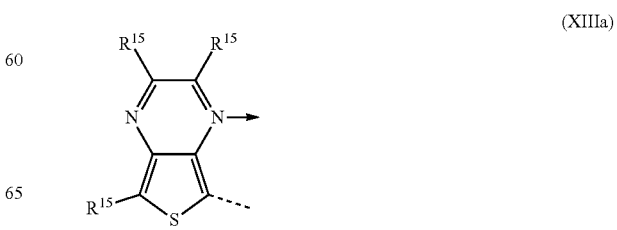

(XIIIa)

13
-continued
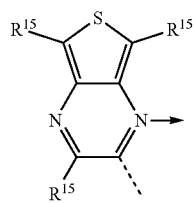
(XIIIb)
14
-continued
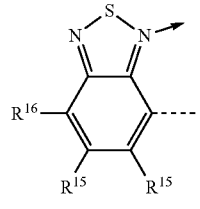
(XIIIc)
Exemplary compounds of formula (I) are:
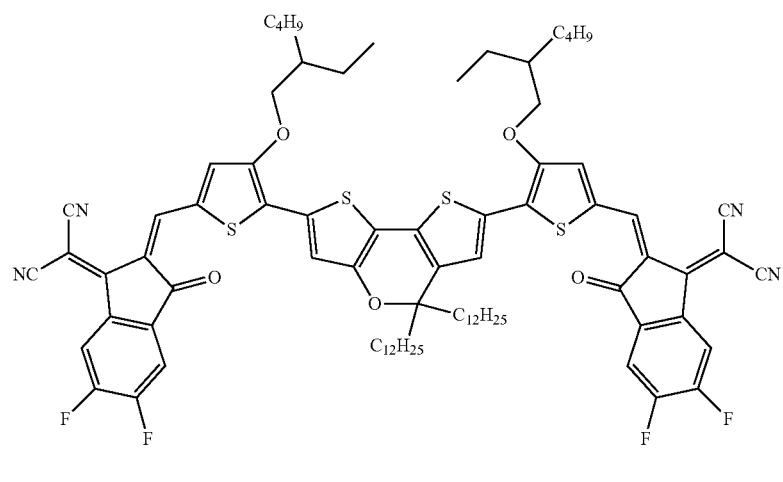
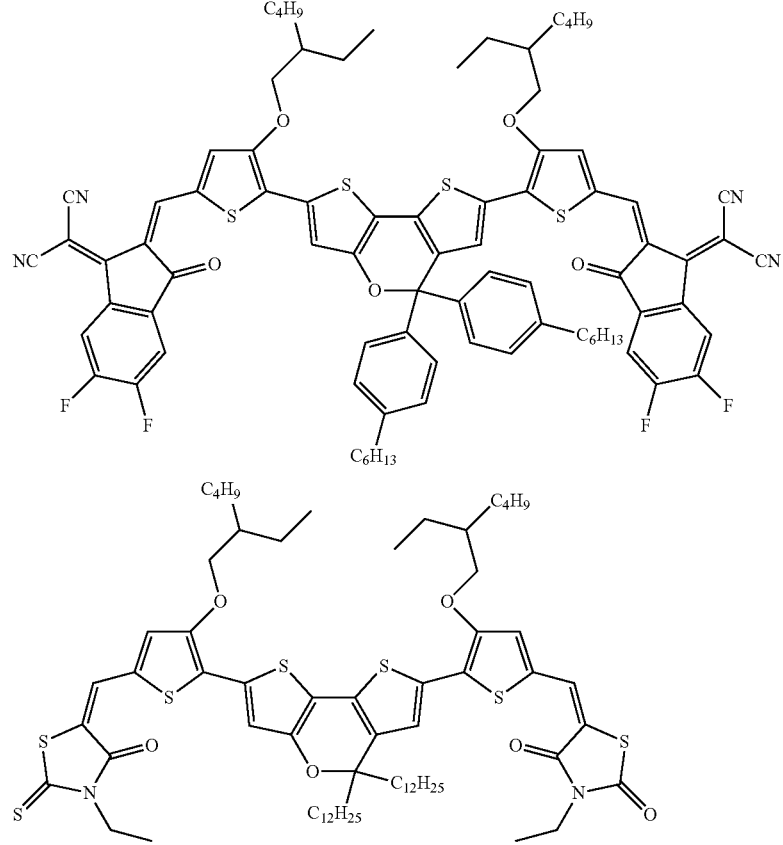

-continued
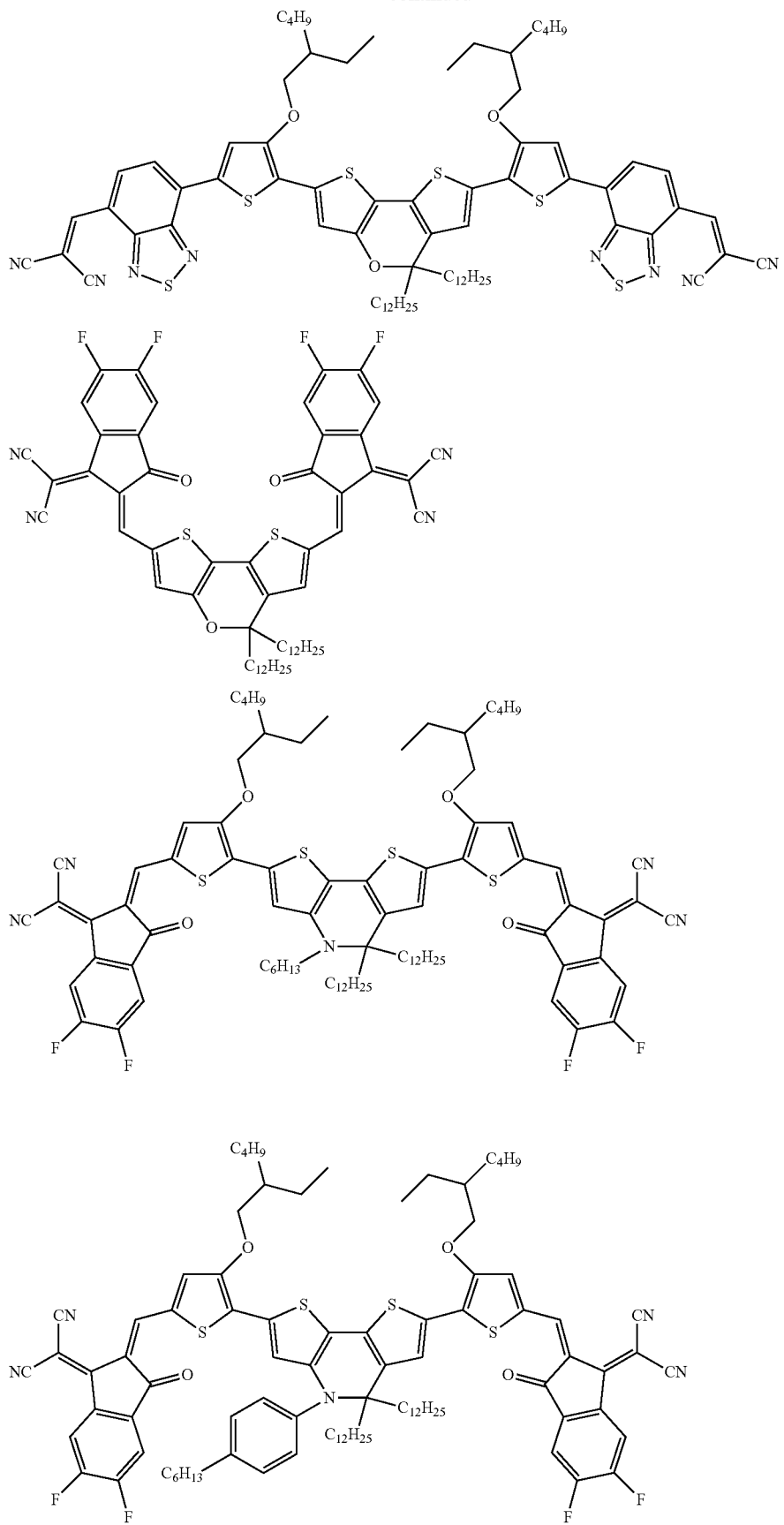

-continued
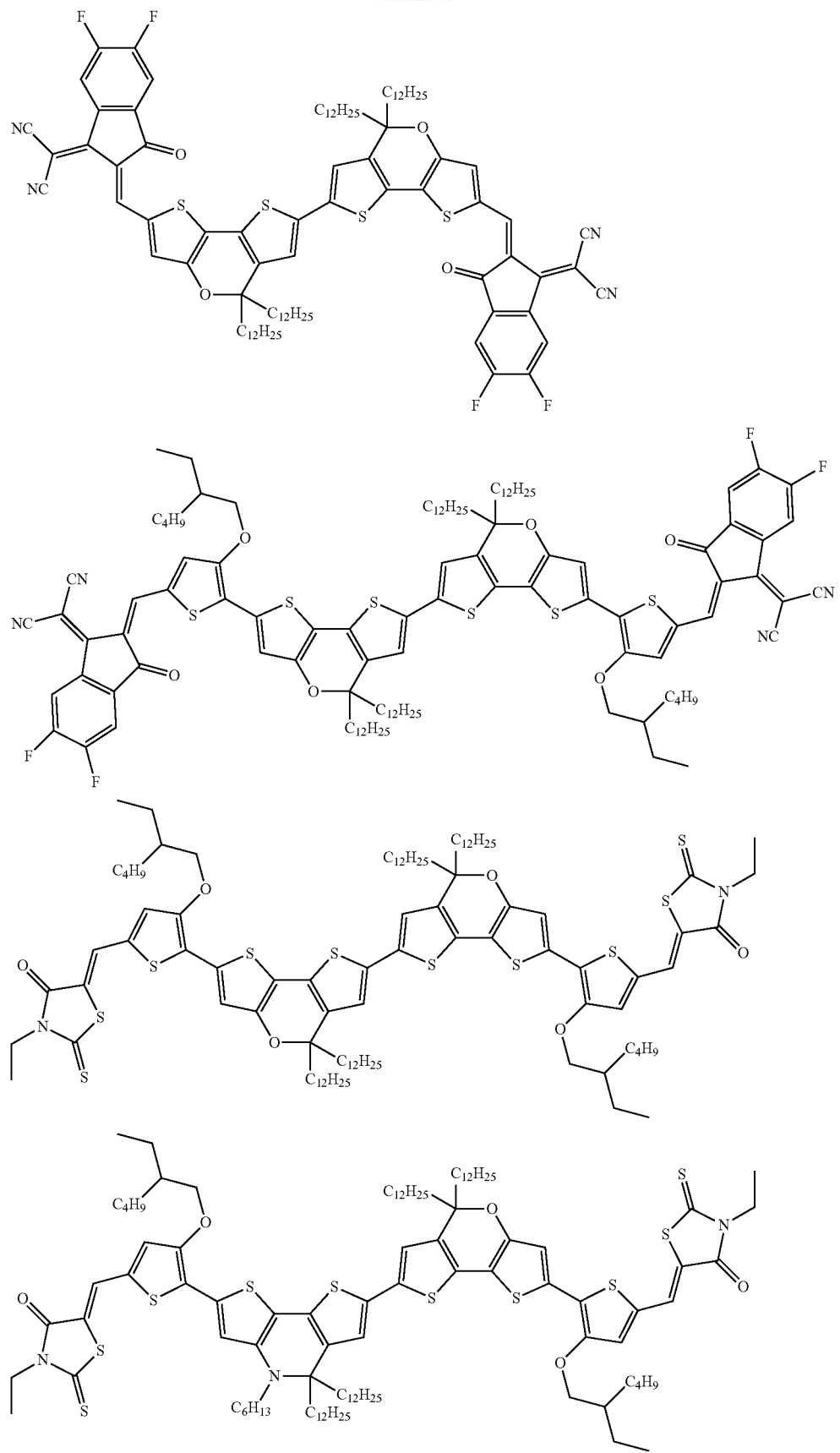

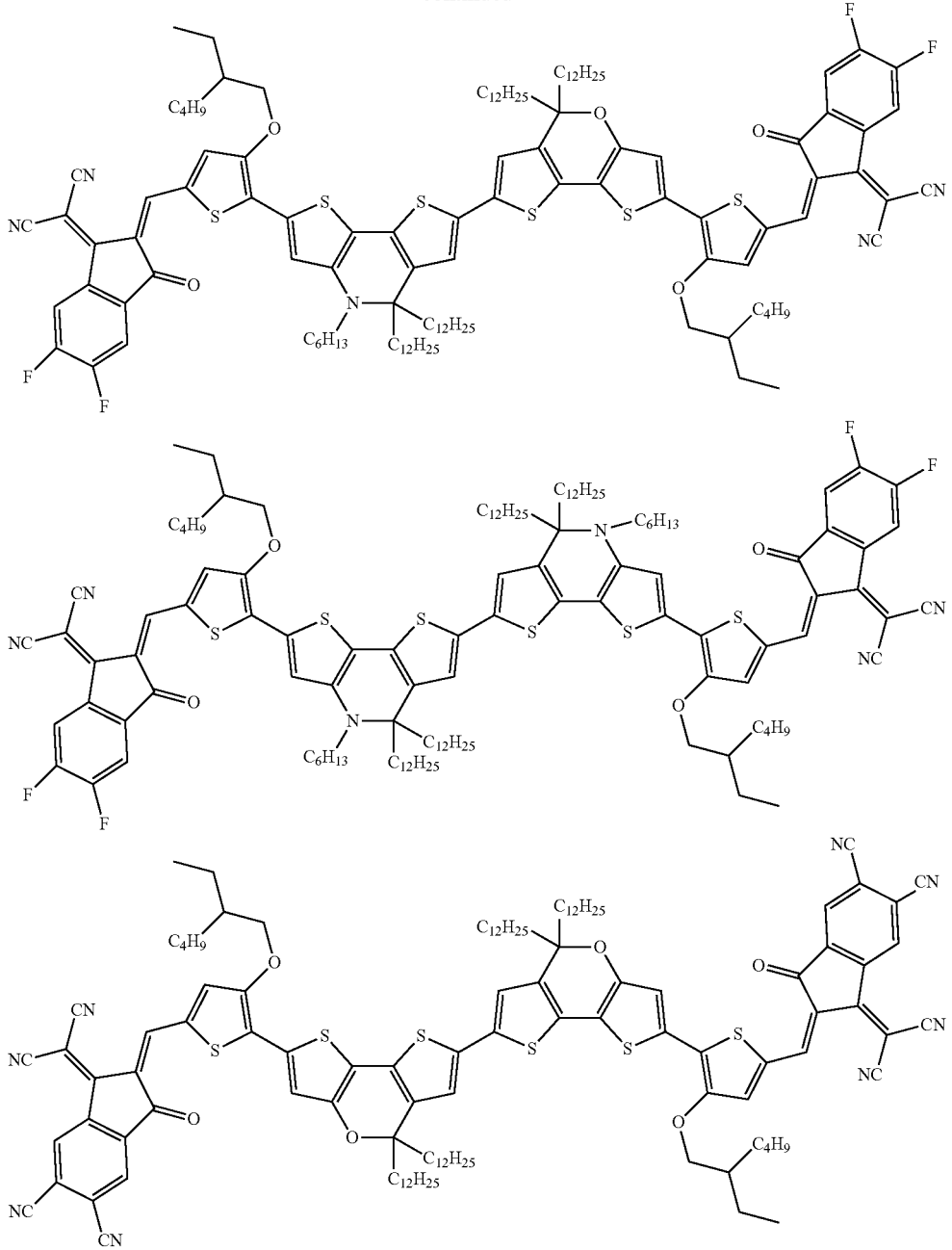

The donor (p-type) compound is not particularly limited and may be selected from electron donating materials that are known to the person skilled in the art, including organic polymers and non-polymeric organic molecules. The p-type compound has a HOMO deeper (further from vacuum) than a LUMO of the compound of formula (I). Optionally, the gap between the HOMO level of the p-type donor and the LUMO level of the n-type acceptor compound of formula (I) is less than 1.4 eV.

In a preferred embodiment the p-type donor compound is an organic conjugated polymer, which can be a homopolymer or copolymer including alternating, random or block copolymers. Preferred are non-crystalline or semi-crystalline conjugated organic polymers. Further preferably the p-type organic semiconductor is a conjugated organic polymer with a low bandgap, typically between 2.5 eV and 1.5 eV, preferably between 2.3 eV and 1.8 eV. As exemplary p-type donor polymers, polymers selected from conjugated hydrocarbon or heterocyclic polymers including polyacene, polyaniline, polyazulene, polybenzofuran, polyfluorene, polyfuran, polyindenofluorene, polyindole, polyphenylene, polypyrazoline, polypyrene, polypyridazine, polypyridine, polytriarylamine, poly(phenylene vinylene), poly(3-substituted thiophene), poly(3,4-bisubstituted thiophene), polyselenophene, poly(3-substituted selenophene), poly(3,4-bisubstituted selenophene), poly(bisthiophene), poly(terthiophene), poly(bisselenophene), poly(terselenophene), polythieno[2,3-b]thiophene, polythieno[3,2-b]thiophene, polybenzothiophene, polybenzo[1,2-b:4,5-b'jdithiophene, polyisothianaphthene, poly(monosubstituted pyrrole), poly (3,4-bisubstituted pyrrole), poly-1,3,4-oxadiazoles, polyisothianaphthene, derivatives and co-polymers thereof may be mentioned. Preferred examples of p-type donors are copolymers of polyfluorenes and polythiophenes, each of which may be substituted, and polymers comprising benzothiadiazole-based and thiophene-based repeating units, each of which may be substituted. It is understood that the p-type donor may also consist of a mixture of a plurality of electron donating materials.

Optionally, the p-type donor has a HOMO level no more than 5.5 eV from vacuum level. Optionally, the p-type donor has a HOMO level at least 4.1 eV from vacuum level.

Unless stated otherwise, HOMO and LUMO levels of a compound as described herein are as measured from a film of the compound using square wave voltammetry.

In some embodiments, the weight of the donor compound to the acceptor compound is from about 1:0.5 to about 1:2.

Preferably, the weight ratio of the donor compound to the acceptor compound is about 1:1 or about 1:1.5.

At least one of the first and second electrodes is transparent so that light incident on the device may reach the bulk heterojunction layer. In some embodiments, both of the first and second electrodes are transparent.

Each transparent electrode preferably has a transmittance of at least 70%, optionally at least 80%, to wavelengths in the range of 400-750 nm or 750-1000 nm or 1000-2000 nm. The transmittance may be selected according to the absorption peak of the compound of formula (I).

In some embodiments, one electrode is transparent, and the other electrode is reflective.

Optionally, the transparent electrode comprises or consists of a layer of transparent conducting oxide, preferably indium tin oxide or indium zinc oxide. In preferred embodiments, the electrode may comprise poly 3,4-ethylenedioxythiophene (PEDOT). In other preferred embodiments, the electrode may comprise a mixture of PEDOT and polystyrene sulfonate (PSS). The electrode may consist of a layer of PEDOT:PSS.

Optionally, the reflective electrode may comprise a layer of a reflective metal. The layer of reflective material may be aluminium or silver or gold. In some embodiments, a bi-layer electrode may be used. For example, the electrode may be an indium tin oxide (ITO)/silver bi-layer, an ITO/aluminium bi-layer or an ITO/gold bi-layer.

The device may be formed by forming the bulk heterojunction layer over one of the anode and cathode supported by a substrate and depositing the other of the anode or cathode over the bulk heterojunction layer.

The area of the OPD may be less than about 3 $cm^2$, less than about 2 $cm^2$, less than about 1 $cm^2$, less than about 0.75 $cm^2$, less than about 0.5 $cm^2$ or less than about 0.25 $cm^2$. The substrate may be, without limitation, a glass or plastic substrate. The substrate can be described as an inorganic semiconductor. In some embodiments, the substrate may be silicon. For example, the substrate can be a wafer of silicon. The substrate is transparent if, in use, incident light is to be transmitted through the substrate and the electrode supported by the substrate.

The substrate supporting one of the anode and cathode may or may not be transparent if, in use, incident light is to be transmitted through the other of the anode and cathode.

The bulk heterojunction layer may be formed by any process including, without limitation, thermal evaporation and solution deposition methods.

Preferably, the bulk heterojunction layer is formed by depositing a formulation comprising the acceptor material and the electron donor material dissolved or dispersed in a solvent or a mixture of two or more solvents. The formulation may be deposited by any coating or printing method including, without limitation, spin-coating, dip-coating, roll-coating, spray coating, doctor blade coating, wire bar coating, slit coating, ink jet printing, screen printing, gravure printing and flexographic printing.

The one or more solvents of the formulation may optionally comprise or consist of benzene substituted with one or more substituents selected from chlorine, $C_{1-10}$ alkyl and $C_{1-10}$ alkoxy wherein two or more substituents may be linked to form a ring which may be unsubstituted or substituted with one or more $C_{1-6}$ alkyl groups, optionally toluene, xylenes, trimethylbenzenes, tetramethylbenzenes, anisole, indane and its alkyl-substituted derivatives, and tetralin and its alkyl-substituted derivatives.

The formulation may comprise a mixture of two or more solvents, preferably a mixture comprising at least one benzene substituted with one or more substituents as described above and one or more further solvents. The one or more further solvents may be selected from esters, optionally alkyl or aryl esters of alkyl or aryl carboxylic acids, optionally a $C_{1-10}$ alkyl benzoate, benzyl benzoate or dimethoxybenzene. In preferred embodiments, a mixture of trimethylbenzene and benzyl benzoate is used as the solvent. In other preferred embodiments, a mixture of trimethylbenzene and dimethoxybenzene is used as the solvent.

The formulation may comprise further components in addition to the electron acceptor, the electron donor and the one or more solvents. As examples of such components, adhesive agents, defoaming agents, deaerators, viscosity enhancers, diluents, auxiliaries, flow improvers colourants, dyes or pigments, sensitizers, stabilizers, nanoparticles, surface-active compounds, lubricating agents, wetting agents, dispersing agents and inhibitors may be mentioned.

The organic photoresponsive device as described herein may be an organic photovoltaic device or an organic photodetector. An organic photodetector as described herein may be used in a wide range of applications including, without limitation, detecting the presence and/or brightness of ambient light and in a sensor comprising the organic photodetector and a light source. The photodetector may be configured such that light emitted from the light source is incident on the photodetector and changes in wavelength and/or brightness of the light may be detected, e.g. due to absorption by, reflection by and/or emission of light from an object, e.g. a target material in a sample disposed in a light path between the light source and the organic photodetector. The sample may be a non-biological sample, e.g. a water sample, or a biological sample taken from a human or animal subject. The sensor may be, without limitation, a gas sensor, a biosensor, an X-ray imaging device, an image sensor such as a camera image sensor, a motion sensor (for example for use in security applications) a proximity sensor or a fingerprint sensor. A 1D or 2D photosensor array may comprise a plurality of photodetectors as described herein in an image sensor.

EXAMPLES

HOMO and LUMO Measurement

HOMO and LUMO values as provided herein are as measured by square wave voltammetry (SWV).

In SWV, the current at a working electrode is measured while the potential between the working electrode and a reference electrode is swept linearly in time. The difference current between a forward and reverse pulse is plotted as a function of potential to yield a voltammogram. Measurement may be with a CHI 660D Potentiostat.

The apparatus to measure HOMO or LUMO energy levels by SWV may comprise a cell containing 0.1 M tertiary butyl ammonium hexafluorophosphate in acetonitrile; a 3 mm diameter glassy carbon working electrode; a platinum counter electrode and a leak free Ag/AgCl reference electrode.

Ferrocene is added directly to the existing cell at the end of the experiment for calculation purposes where the potentials are determined for the oxidation and reduction of ferrocene versus Ag/AgCl using cyclic voltammetry (CV).

The sample is dissolved in Toluene (3 mg/ml) and spun at 3000 rpm directly on to the glassy carbon working electrode.

LUMO=4.8–$E$ ferrocene (peak to peak average)–$E$ reduction of sample (peak maximum).

HOMO=4.8–$E$ ferrocene (peak to peak average)+$E$ oxidation of sample (peak maximum).

A typical SWV experiment runs at 15 Hz frequency; 25 mV amplitude and 0.004 V increment steps. Results are calculated from 3 freshly spun film samples for both the HOMO and LUMO data.

Absorption Measurement

Absorption spectra as described herein are as measured from a 15 microgram/ml solution using a Cary 5000 UV-vis-IR spectrometer.

Synthesis

Compounds of formula (I) may be prepared according to the following reaction schemes:

Scheme 1

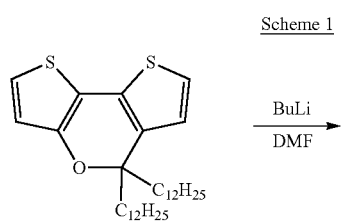

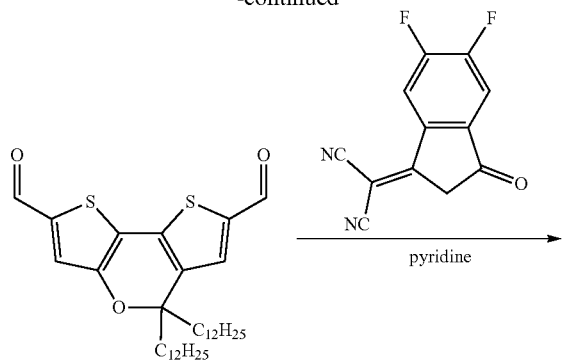

-continued

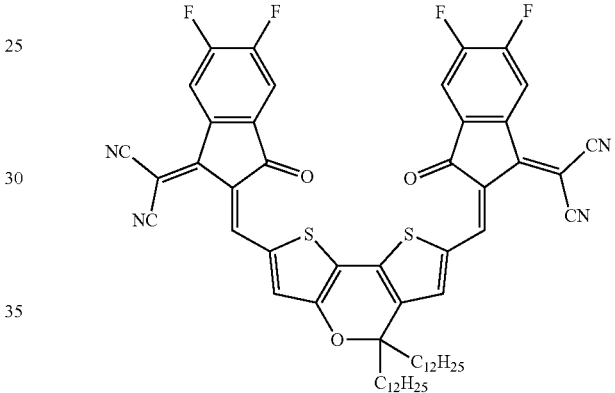

Scheme 2

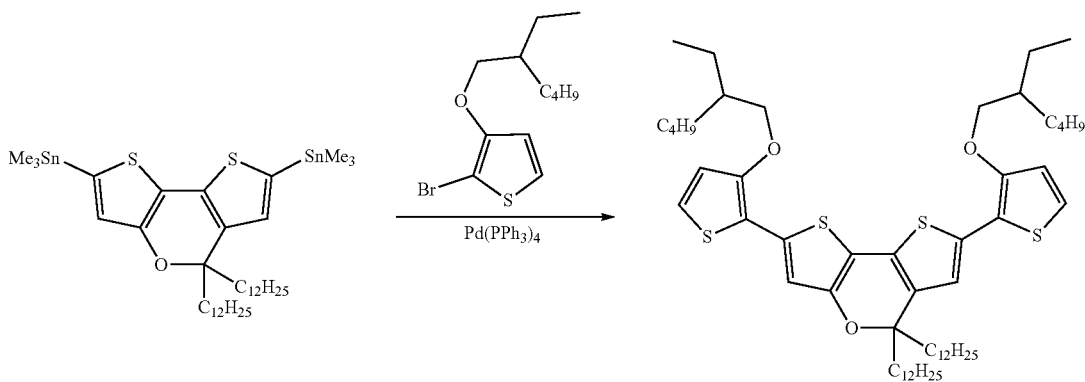

-continued
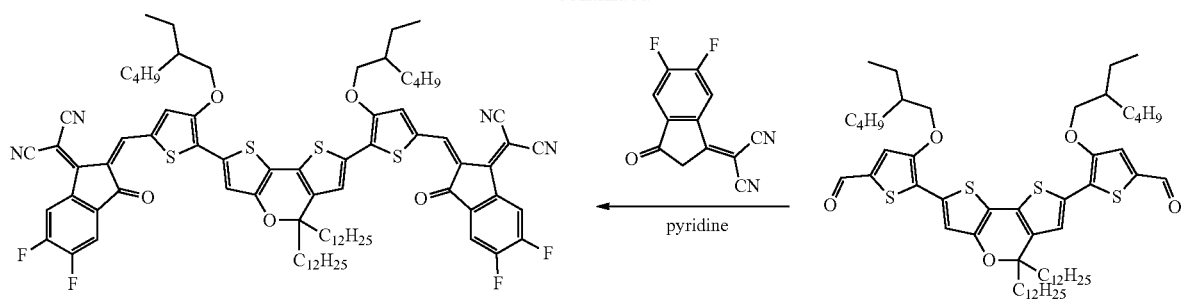
Scheme 3
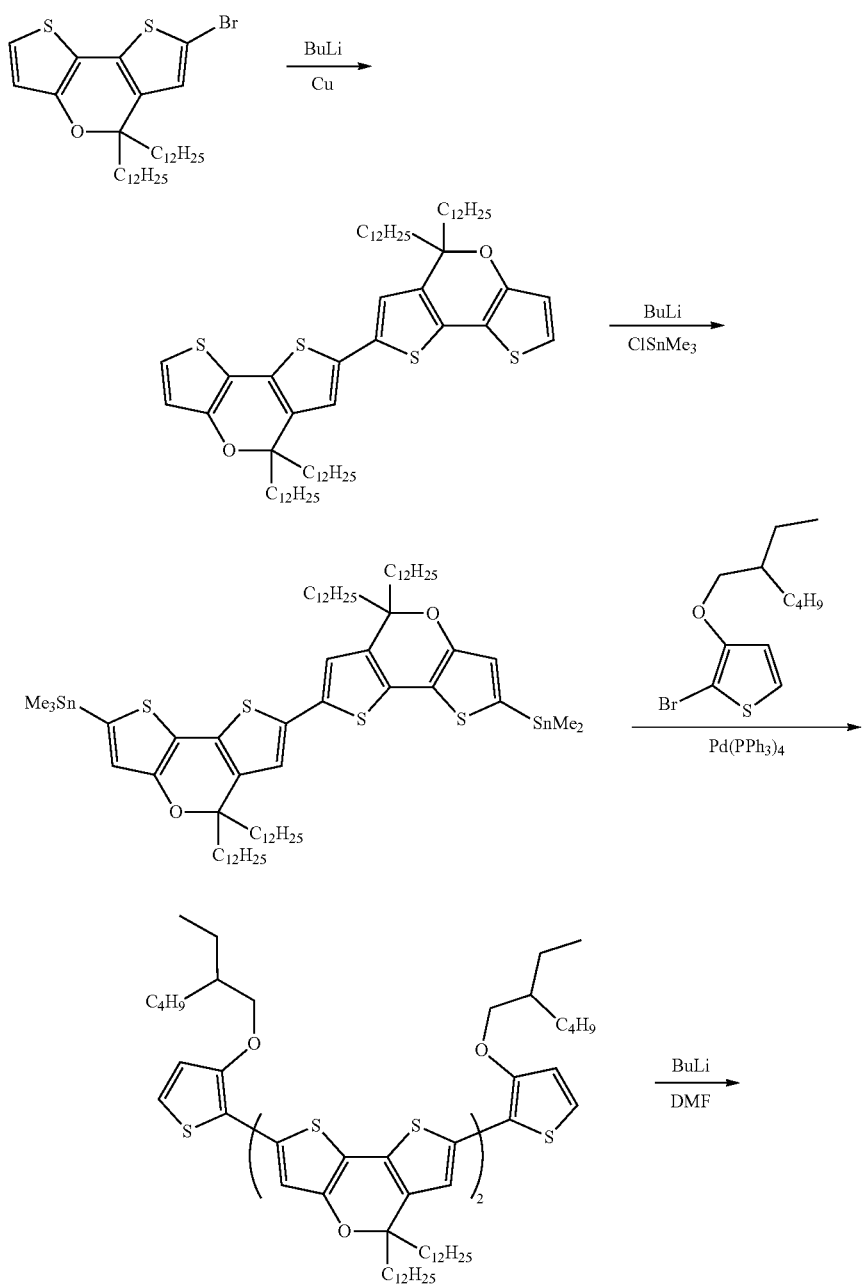

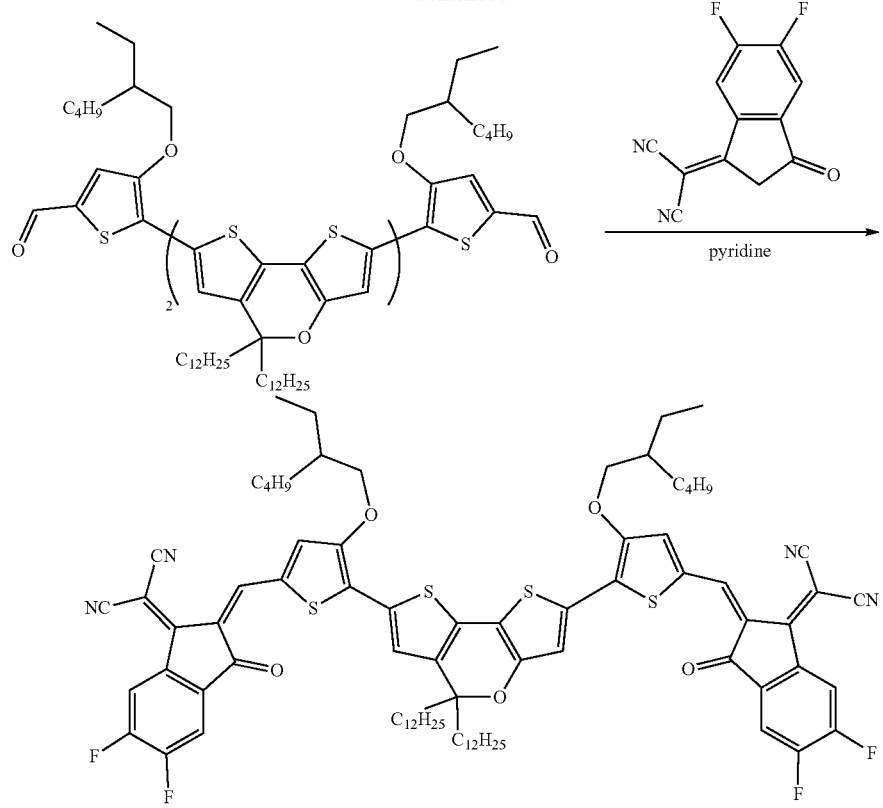

Compound Example 1

Compound Example 1 was prepared according to the following reaction scheme:

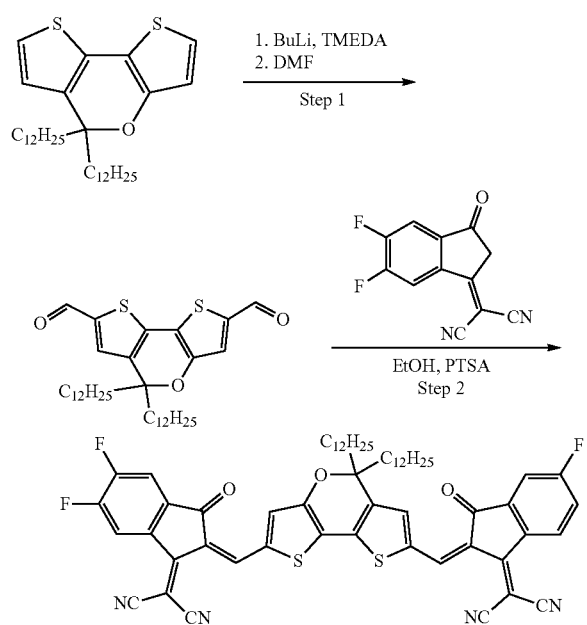

Compound Example 1

Step 1: 5,5-didodecyl-5H-dithieno[3,2-b:2',3'-d] pyran-2,7-dicarbaldehyde 5,5-didodecyl-5H-dithieno[3,2-b:2',3'-d]pyran (1 g, 1.88 mmol) and N,N,N',N'-tetramethyl ethylene diamine (1.88 mmol, 0.28 mL) were dissolved in 15 mL of dry THF under nitrogen. The solution was cooled down to −78° C. To this solution n-BuLi (2.5 M, 4.65 mmol, 1.86 mL) was added dropwise. The reaction mixture was left stirring at −78° C. for 1 hour, afterwards dry DMF (5.27 mmol, 0.41 mL) was added to the reaction mixture dropwise. The reaction was left stirring overnight, allowing the temperature to go up to room temperature. The reaction mixture was quenched with 50 mL of water and extracted with ethyl acetate. The organic layer was dried over $MgSO_4$ and then solvent was removed under reduced pressure. The compound was purified on silica gel column using a mixture of dichloromethane (25-45%) and heptane as an eluent. The product-containing fractions were combined and concentrated under reduced pressure to yield a product as bright orange oil (0.8 g) with 97.3% HPLC purity.

H-NMR ($CDCl_3$): 9.86 (s, 1H), 9.82 (s, 1H), 7.36 (s, 1H), 7.29 (s, 1H), 1.82-1.96 (m, 4H1), 1.3-1.4 (m, 2H1), 1.3-1.1 (m, 38H), 0.83-0.9 (m, 6H1).

Step 2

To a solution of 5,5-didodecyl-5H-dithieno[3,2-b:2',3'-d] pyran-2,7-dicarbaldehyde (0.49 mmol, 0.29 g) in ethanol (135 mL) under nitrogen, p-toluene sulfonic acid (4.86 mmol, 0.92 g) and IC-2F (3.88 mmol, 0.89 g) were added. This reaction mixture was heated to 65° C. overnight. The product was filtered off, washed with ethanol and loaded onto reverse phase silica gel column (as a solid on isolute). The fractions were eluted using a 1:1.5 mixture of THF:Acetonitrile. The fractions containing the product were combined and concentrated in vacuum to yield a dark blue product (87 mg) with 98.89% HPLC purity.

H-NMR (CDCl$_3$): 8.83 (s, 1H), 8.75 (s, 1H), 8.52-8.6 (m, 2H), 7.7-7.76 (m, 2H), 7.38-7.42 (m, 2H), 1.86-2 (m, 4H), 1.32-1.4 (m, 2H), 1.17-1.3 (m, 38H), 0.85 (t, J=7.16 Hz, 6H).

Compound Example 1 has a HOMO level of 5.79 eV and a LUMO level of 4.18 eV as measured by square wave voltammetry as described herein, giving a band gap of 1.61 eV.

Compound Example 2

Compound Example 2 was prepared by linking a fused electron-donating group to a thiophene bridging group and linking the thiophene bridging group to IC-2CN to form the electron-accepting group.

IC-2CN was formed according to the following reaction scheme:

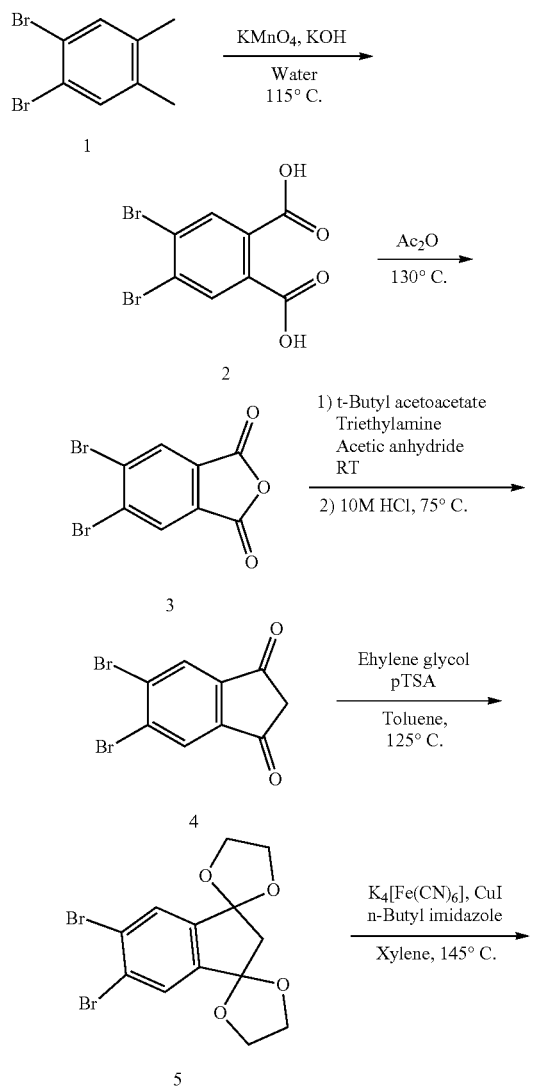

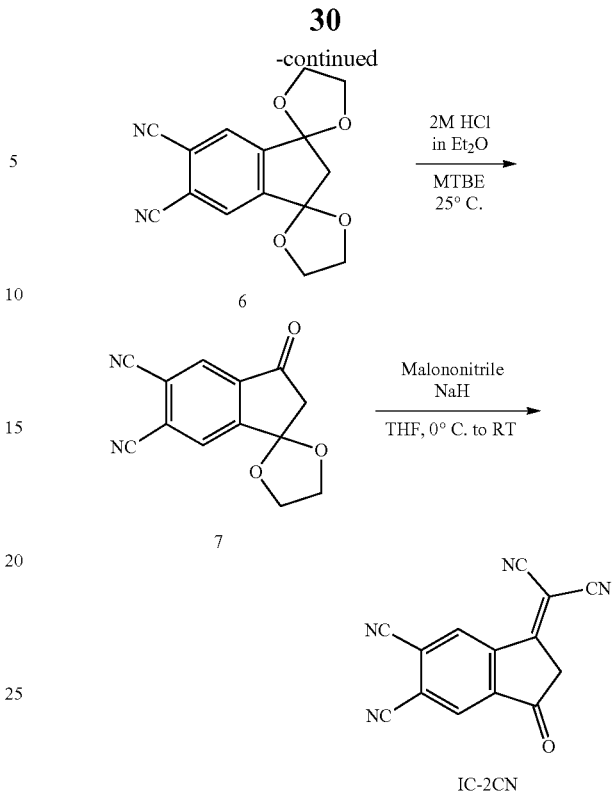

Intermediate 2

1,2-dibromo-4,5-dimethylbenzene (100 g, 0.38 mol), potassium hydroxide (105 g, 1.89 mol) and potassium permanganate (298 g, 1.89 mol) were mixed with water (2 L) and the reaction mixture heated at 115° C. for 24 hours. After cooling to room temperature, sodium bisulphite was added, the pH was adjusted to 8 using 10% potassium hydroxide solution and the mixture was filtered through a celite pad which was washed with water (2×50 ml). The aqueous layer was acidified to a pH of 1 with concentrated HCl to give a white precipitation which was filtered, washed with water (2×250 ml) and triturated with methanol. The resulting solid was filtered and dried under vacuum to give Intermediate 2 (46 g, 38% yield).

$^1$H-NMR (400 MHz, DMSO-d6): δ [ppm] 8.18 (s, 2H).

Intermediate 3

Intermediate 2 (200 g, 618 mmol) in acetic anhydride (I L) was heated at 130° C. for 4 hours. After cooling to room temperature, the crude solid was filtered, washed with toluene (200 ml) and dried under vacuum to give Intermediate 3 (200 g).

Intermediate 4

Tert-butylaceto acetate (103 g, 654 mmol) was added to a mixture of Intermediate 4 (200 g, 654 mmol), acetic anhydride (1 L) and triethyl amine (600 ml) and the reaction mixture stirred at 25° C. for 16 hours. After quenching with a mixture of 1 L (10 M HCl) and ice (1 kg) while maintaining the temperature below 50° C., the mixture was heated to 75° C. for 2 hours and cooled to room temperature. The solid was filtered and was dried to give Intermediate 4 as a brown solid (132 g, 68% yield).

LCMS: 96.8% purity.

$^1$H-NMR (400 MHz, DMSO-d6): δ [ppm] 3.28 (s, 2H), 8.25 (s, 2H).

Intermediate 5

A solution of Intermediate 4 (120 g, 394 mmol), ethylene glycol (244 g, 3.9 mol) and para-toluenesulfonic acid (6.78 g, 39.4 mmol) in toluene (1.5 L) was heated at 125° C. for 40 hours. After cooling to room temperature, the reaction mixture was added to water (500 ml), the organic layer was separated and concentrated under vacuum. The crude residue was suspended in hexane (1 L), stirred for 30 minutes and filtered to give Intermediate 5 (91 g 59% yield).

$^1$H-NMR (400 MHz, CDCl$_3$): δ [ppm] 2.56 (s, 2H), 4.09-4.12 (m, 4H), 4.20-4.24 (m, 4H), 7.65 (s, 2H).

Intermediate 6

Potassium ferrocyanide (48.6 g, 132.0 mmol), 1-butyl imidazole (42.9 g, 383.8 mmol) and Copper (I) iodide (12.5 g, 65.6 mmol) were added in three portions to a solution of Intermediate 5 (65 g, 165.8 mmol) in o-xylene (2.5 L). After heating at 140° C. for 44 hours, the reaction mixture was cooled to room temperature, filtered through Florisil plug, and washed with toluene followed by ethyl acetate. The filtrate was concentrated under reduced pressure to 1 L and stirred at 25° C. for 16 hours. The resulting solid was filtered, washed with hexanes and purified by column chromatography (silica 60-120 mesh, hexanes:ethyl acetate (2:8) as eluent). Fractions containing the desired product were concentrated under reduced pressure, hexane (1 L) was added to the residue, and the resulting was filtered and dried under vacuum to give Intermediate 6 (30 g, 64% yield).

HPLC: 98.9% purity.

$^1$H-NMR (400 MHz, CDCl$_3$): δ [ppm] 2.62 (s, 2H), 4.15-4.21 (m, 4H), 4.24-4.28 (m, 4H), 7.83 (s, 2H).

Intermediate 7

Hydrogen chloride in diethyl ether (2 M, 500 ml, 1.0 mol) and water (5 ml) were added to a solution of Intermediate 6 (90 g, 316.6 mmol) in tert-butyl methyl ether (1 L). After stirring at 25° C. for 48 hours. the mixture was filtered, the resulting solid washed with diethyl ether (100 ml×3) and stirred 3 times with acetone (500 ml) for 1 hour and filtered. The resulting solid was dried under vacuum to give Intermediate 7 (61 g, 80% yield).

HPLC: 95% purity.

1H-NMR (400 MHz, CDCl$_3$): δ [ppm] 3.07 (s, 2H), 4.20-4.36 (m, 4H), 8.11 (s, 1H), 8.16 (s, 1H).

IC-2CN

A solution of malononitrile (5.49 g, 83.2 mmol) in THF (200 ml) was added to a suspension of sodium hydride (3.31 g, 83.2 mmol) in THF (200 ml) at 25° C. and stirred at 25° C. for an hour. The resulting mixture was added to a suspension of Intermediate 7 (20 g, 83.2 mmol) in THF (600 mL) at 0° C., and the reaction mixture stirred at 25° C. for 16 hours. The resulting mixture was concentrated under vacuum to give crude product as dark purple solid. This procedure was repeated on another 40 g of intermediate 7. The crude material was combined and purified twice by column chromatography (silica gel 230-400 mesh, 10 to 20% MeOH in DCM as eluent).

Fractions containing the desired product were combined, concentrated under reduced pressure and the residue stirred in a mixture of dichloromethane and acetonitrile to give IC-2CN (20.2 g, 33% yield).

LCMS: 96.35% purity.

$^1$H-NMR (400 MHz, CD3OD): δ [ppm] 3.61 (s, 2H), 5.55 (s, 1H), 7.73 (s, 1H), 8.29 (s, 1H).

The fused electron-donating group was formed according to the following reaction scheme:

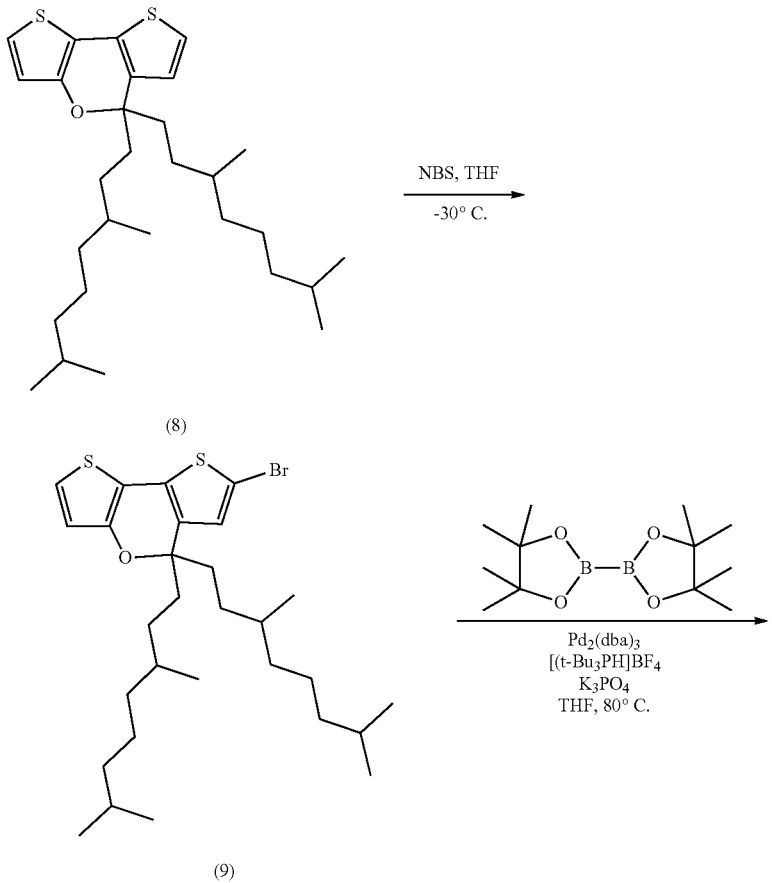

-continued
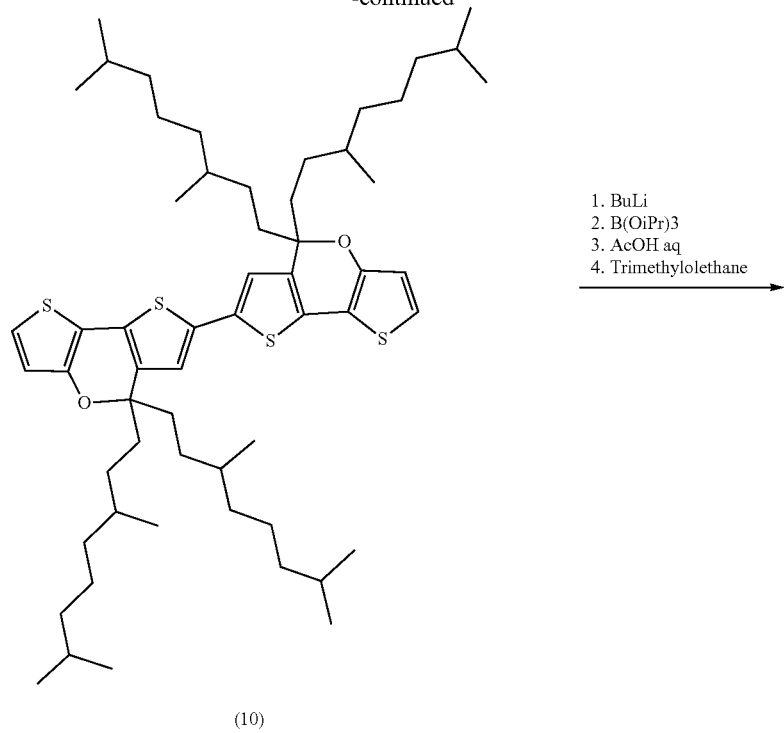
(10)
1. BuLi
2. B(OiPr)3
3. AcOH aq
4. Trimethylolethane
→
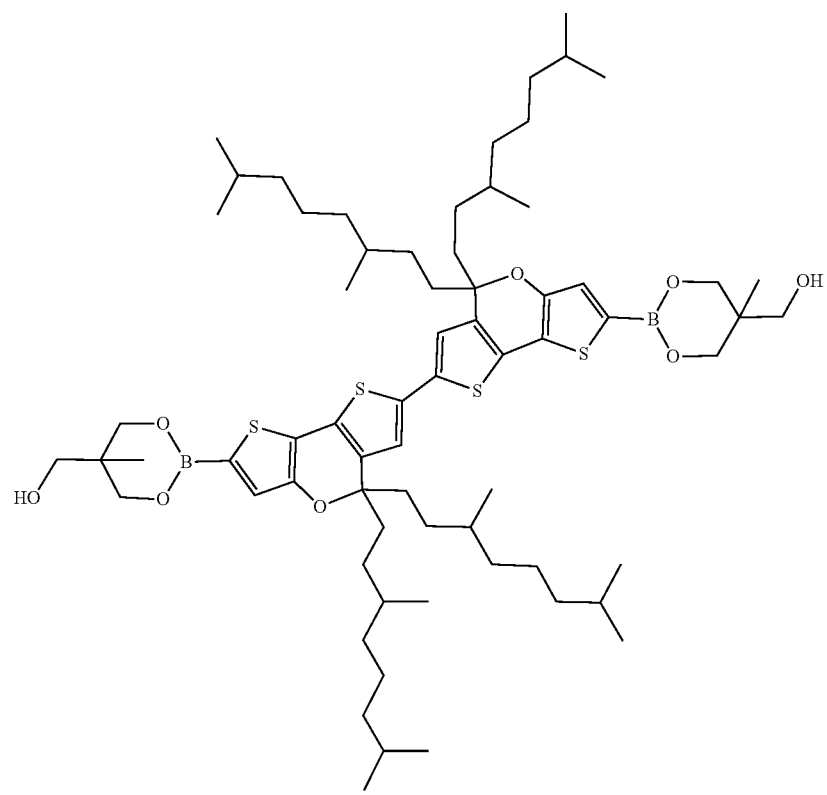
(11)

Compound (8) was synthesised as described in WO2013005569, the contents of which are incorporated herein by reference.

Compound (9)

N-bromosuccinimide (1.71 g, 9.58 mmol) was added to a solution of Compound (8) (5 g, 10.53 mmol) in THF (105 ml) at −30° C. added portion. After stirring at −30° C. for 1 hour, the reaction mixture was quenched at room temperature with sodium thiosulfate solution and extracted with heptane, dried over magnesium sulfate and concentrated under reduced pressure to give Compound (9) as a yellow oil (6.1 g).

HPLC: 94.1% purity.

Compound (10)

Potassium phosphate tribasic solution (3 M aqueous, 50 ml, 150 mmol) was added to a solution of (Compound 9) (6.11 g, 11.03 mmol) in THF (50 ml) and Nitrogen was bubbled through the mixture for 30 minutes. Tris(dibenzylideneacetone)dipalladium(0) (0.4 g, 0.44 mmol), tri-tert-butylphosphonium tetrafluoroborate (0.51 g, 1.76 mmol) and bis(pinacolato)diboron (1.4 g, 5.51 mmol) were added and the mixture was heated at 80° C. for 20 hours. After cooling to room temperature, the reaction mixture was extracted with ethyl acetate, the combined organic phases were washed with water, dried with magnesium sulfate and concentrated under reduced pressure. The residue was purified by column chromatography (silica gel KP-Sil 340 g, heptane as eluent). Fractions containing the desired product were combined and concentrated under reduced pressure to give Compound (10) as an oil (4.57 g, 87% yield).

HPLC: 99.19% purity.

Compound (11)

N,N,N',N'-tetramethylethylenediamine (0.32 ml, 2.11 mmol) was added to a solution of Compound (10) (2 g, 2.11 mmol) in THF (16 ml), the mixture was cooled to −78° C. and n-BuLi (2.5 M, 2.09 ml, 5.21 mmol) was added dropwise. The mixture was stirred at −78° C. for 2 hours, triisopropylborate (1.36 ml, 5.91 mmol) was added dropwise and the mixture was stirred for a further hour at −78° C. After warming to above 0° C. a degassed solution of acetic acid (11% in water, 23 ml) was added, the mixture stirred for 10 mins and degassed toluene (40 ml) was added. The layers were allowed to separate, and the water removed with a syringe. Trimethylolethane (0.76 g, 6.33 mmol) and magnesium sulfate (13 g) were added and the mixture stirred overnight at room temperature, filtered through a celite plug and concentrated under reduced pressure. The residue was recrystallised from a toluene and heptane mixture and the resulting solid was dried under vacuum to give Compound (11) as an orange solid, (2 g, 79% yield).

HPLC: 97.98% purity.

Compound Example 2 was prepared according to the following reaction scheme:

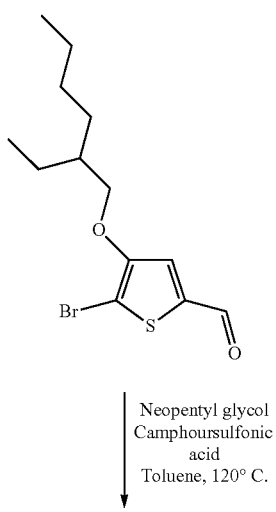

-continued
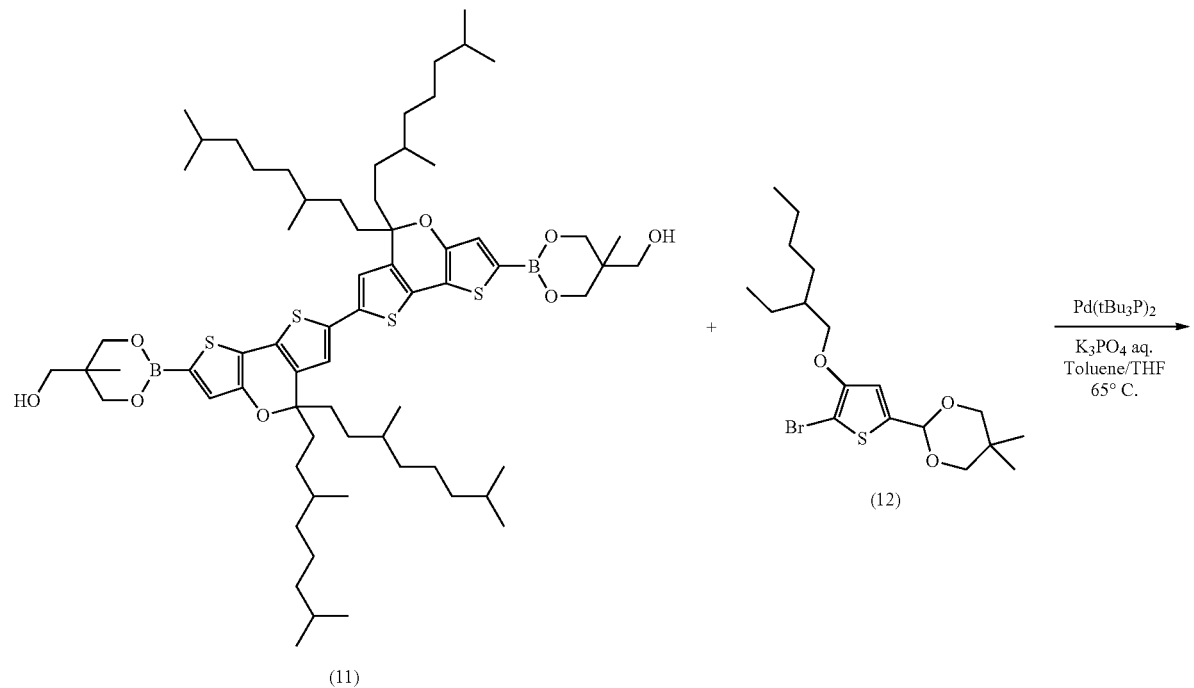
(11)
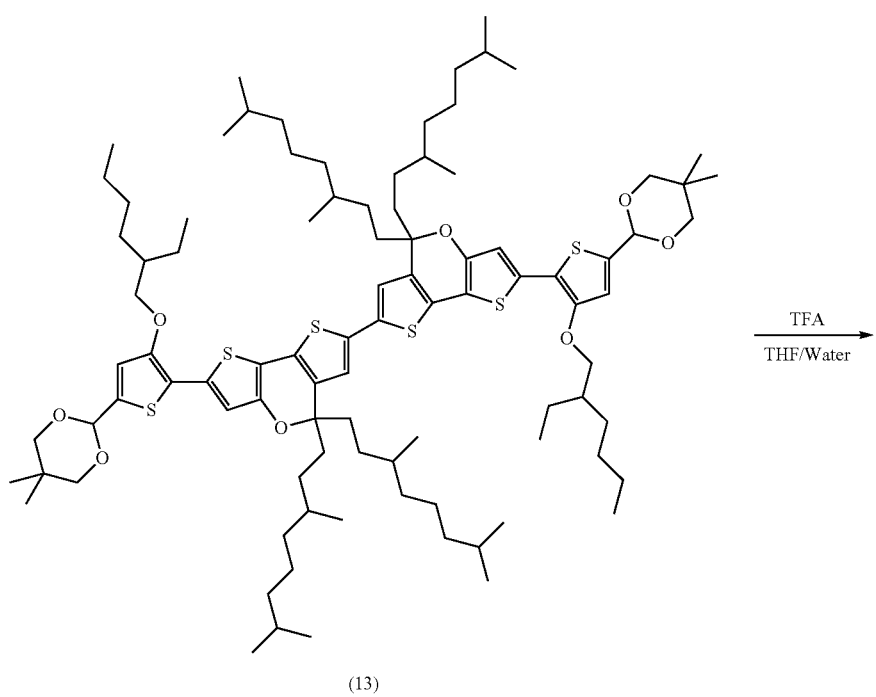
(13)

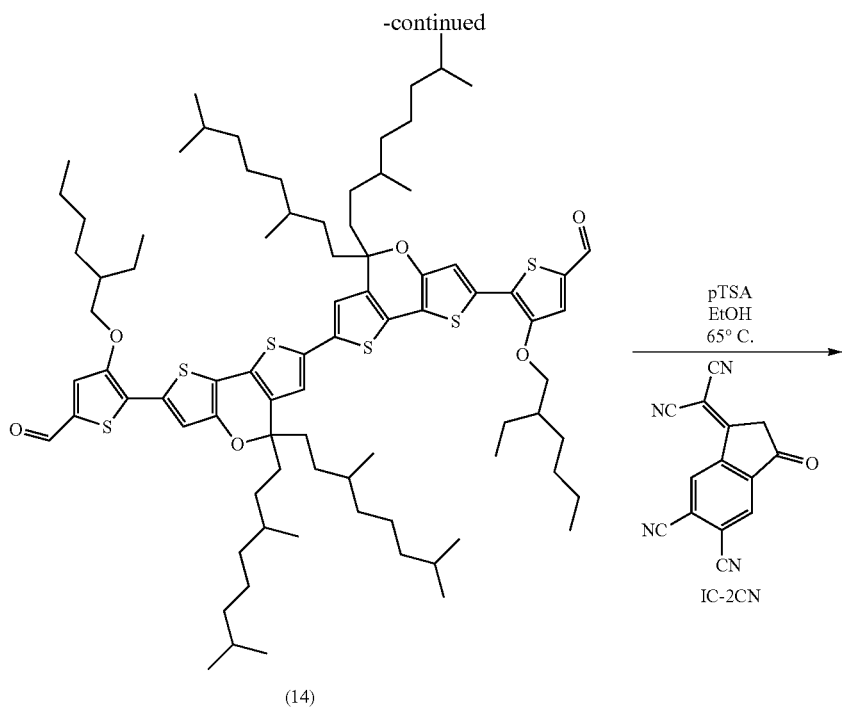

(14)

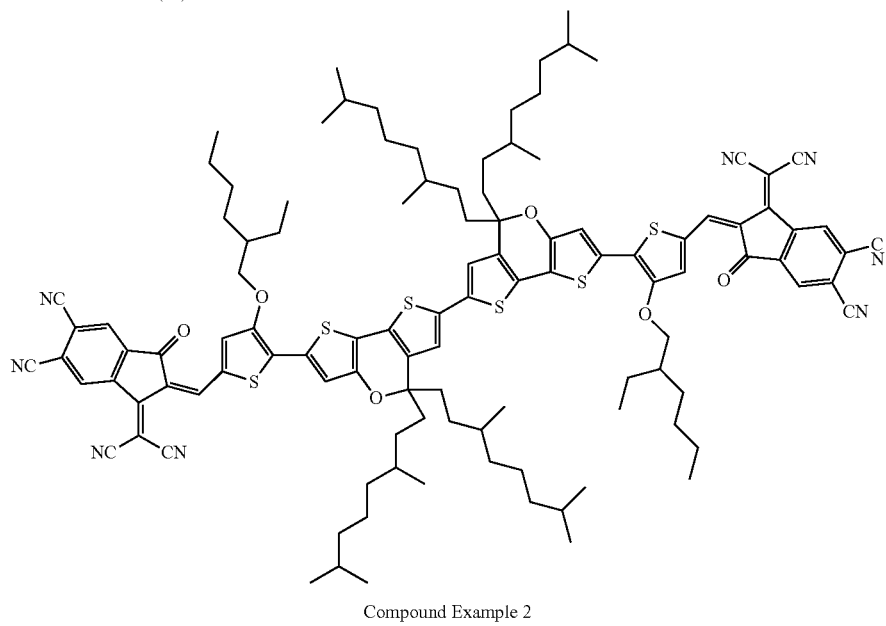

Compound Example 2

5-Bromo-4-((2-ethylhexyl)oxy)thiophene-2-carbaldehyde was synthesised as described in the Journal of Materials Chemistry A: Materials for Energy and Sustainability (2020), 8(10), p 5163-5170.

Compound (12)

A mixture of 5-bromo-4-((2-ethylhexyl)oxy)thiophene-2-carbaldehyde (20 g, 626.4 mmol), neopenyl glycol (13 g, 125.2 mmol) and camphorsulfonic acid (0.7 g, 3.0 mmol) in toluene (800 ml) was heated to 120° C. and stirred for 2 hours. After cooling to room temperature, water (100 ml) was added, the mixture extracted with diethyl ether (2×200 ml), the combined organics layer washed with brine (200 ml) and dried over sodium sulphate and concentrated. The crude product was purified by column chromatography (silica gel 230-400 mesh, 5% ethyl acetate in petroleum ether as eluent) to give the product as a yellow oil (15.4 g, 61 & yield).

HPLC: >99% purity.

1H-NMR (400 MHz, DMSO-d6): δ [ppm] 0.74 (s, 3H), 0.86-0.91 (m, 6H), 1.13 (s, 3H), 1.33-1.47 (m, 8H), 1.57-1.62 (m, 1H), 3.59-3.66 (m, 4H), 3.91 (d, J=6.0 Hz, 2H), 5.59 (s, 1H), 7.06 (s, 1H).

Compound (13)

Water (45 ml) was added to a solution of Compound (11) (1.50 g, 1.24 mmol) and Compound (12) (1.50 g, 3.72 mmol) dissolved in degassed THF (30 ml) and toluene (50 ml). Bis(tri-tert-butylphosphine)palladium(0) (25.3 mg, 0.050 mmol) was added to the reaction mixture using toluene, the flask was placed in a oil bath heated to 65° C.

and degassed potassium phosphate tribasic (2.61 g, 12.3 mmol) in water (5 ml) was added and the mixture was stirred at this temperature for 3.5 hours. After cooling to room temperature and diluting with toluene and water, the organic phase was separated and washed with water, dried over magnesium sulfate and concentrated to dryness under reduced pressure. The residue was filtered through a silica plug, eluted with a mixture of dichloromethane and heptane (1:1) and concentrated to dryness to give Compound (13) as a dark red oil (2.4 g).

Compound (14)

To a solution of Compound (13) (1.97 g, 1.23 mmol) in THF (50 ml) was added water (20 ml) and trifluoroacetic acid portion wise between 15° C. and 27° C. After stirring at room temperature for 1 hour the mixture was poured into ice/water (150 ml), extracted with toluene (100 ml) and the organic phase was washed with a saturated solution of sodium bicarbonate (2×50 ml) and water (3×50 ml), dried over magnesium sulfate and concentrated to dryness under reduced pressure. The crude product was purified by column chromatography (silica gel, DCM-heptane as eluent), the fractions containing the desired product we concentrated and the residue suspended in methanol and filtered to give Compound (14) as a deep purple solid (0.87 mg, 50% yield).

HPLC: 92.39% purity

Compound Example 2

A mixture of Compound (14) (0.87 g, 0.61 mmol), IC-2CN (0.75 g, 3.1 mmol), para-toluenesulfonic acid monohydrate (0.87 g, 4.6 mmol), toluene (15 ml) and ethanol (30 ml) was heated at 65° C. for 1 hour. After cooling to room temperature, the crude product was filtered and purified by column chromatography (silica gel, heptane-ethyl acetate, DCM and DCM-THF as eluents). Fractions containing the desired product were combined. concentrated under reduced pressure, dissolved in THF and added dropwise to ethanol (200 ml). The resulting solid was dried under vacuum to give Compound Example 2 as a dark blue solid (63 mg, 54% yield).

HPLC: 93.0% purity.

Compound Example 2 has a peak maximum absorption as measured by UV-vis absorption spectroscopy of 1053 nm in film and 948 nm is solution.

HOMO and LUMO levels of a film of Compound Example 2 and comparative compound IEICO-4F as measured by square wave voltammetry are provided in Table 1.

IEICO-4F

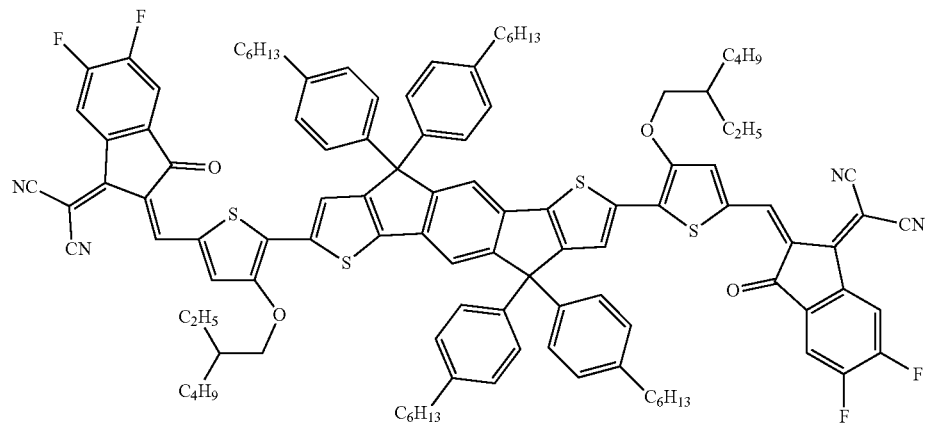

TABLE 1

| Compound | HOMO (eV) | LUMO (eV) | Eg (eV) |
|---|---|---|---|
| Compound Example 2 | 5.20 | 4.19 | 1.01 |
| IEICO-4F | 5.44 | 4.04 | 1.40 |

Modelling Data—Electron Withdrawing Groups and Electron Accepting Groups

LUMO levels of certain electron donating groups of formula (II) were modelled and results are set out in Table 1 in which each bond to an electron-accepting group of formula (I), indicated by a wavy line in Table 2, was replaced with bonds to H.

LUMO levels of certain electron accepting groups are included for comparison.

Quantum chemical modelling was performed using Gaussian09 software available from Gaussian using Gaussian09 with B3LYP (functional) and LACVP* (Basis set).

TABLE 2
| Group | Structure | LUMO/eV |
|---|---|---|
| EDG | 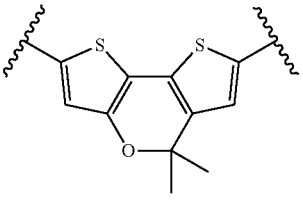 [SMILES: *c1cc2c(s1)-c1sc(*)cc1C(C)(C)O2] | −1.094 |
| EDG | 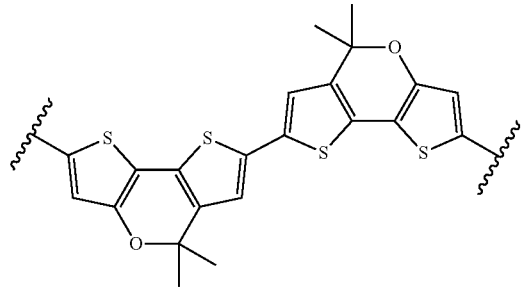 [SMILES: *c1cc2c(s1)-c1sc(-c3cc4c(s3)-c3sc(*)cc3OC4(C)C)cc1C(C)(C)O2] | −1.758 |
| EAG | 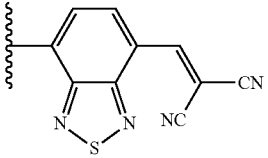 [SMILES: *c1ccc(C=C(C#N)C#N)c2nsnc12] | −3.553 |
| EAG | 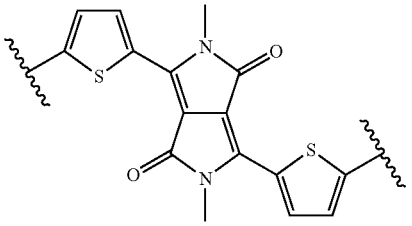 [SMILES: *c1ccc(C2=C3C(=O)N(C)C(c4ccc(*)s4)=C3C(=O)N2C)s1] | −2.475 |
| EAG | 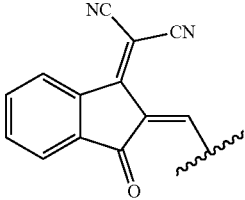 [SMILES: */C=C1\C(=O)c2ccccc2C1=C(C#N)C#N] | −3.379 |
| EAG | 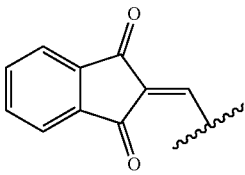 [SMILES: *C=C1C(=O)c2ccccc2C1=O] | −2.462 |
| EAG | 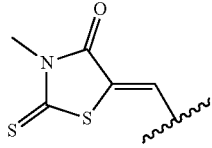 [SMILES: */C=C1\SC(=S)N(C)C1=O] | −2.509 |

Modelling Data—Compounds of Formula (I)
HOMO and LUMO levels of the following compounds were modelled as described above and results are set out in Table 3.
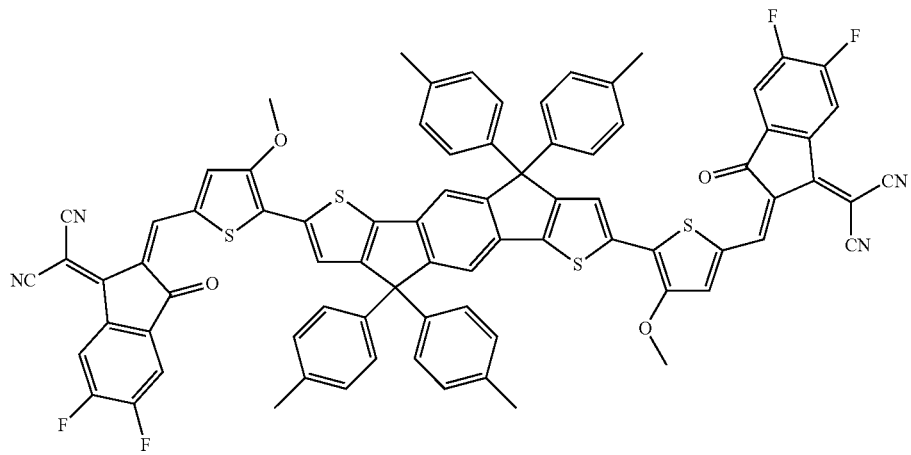
Model Comparative Compound 1A
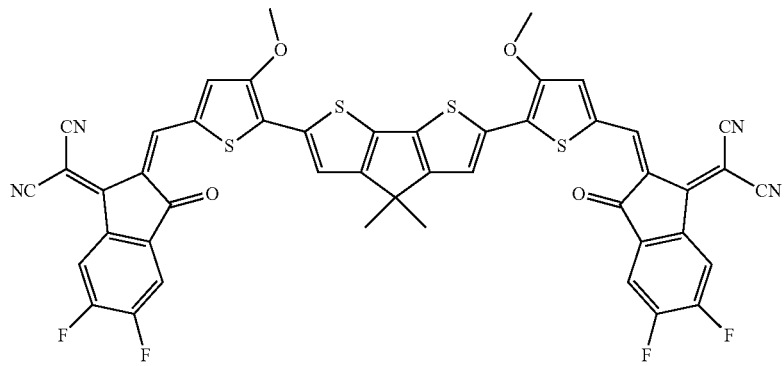
Model Comparative Compound 1B
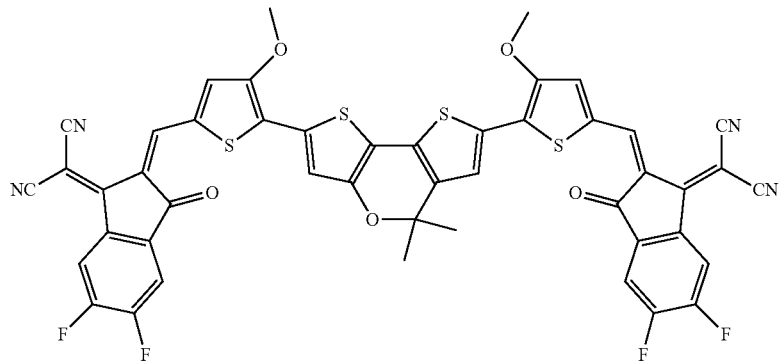
Model Compound Example 1

Model Comparative Compound 2A
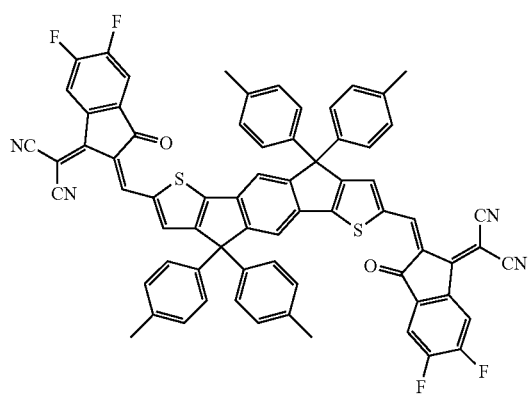
Model Comparative Compound 2B
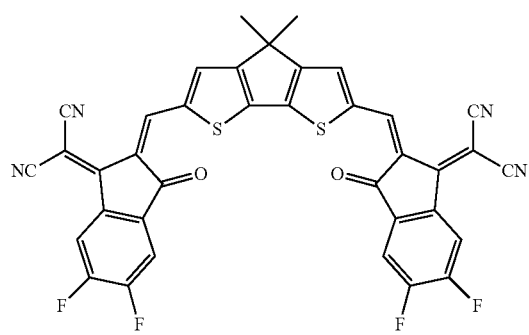
Model Compound Example 2
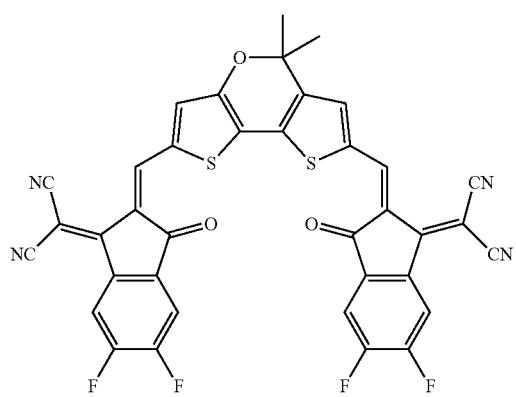
Model Comparative Compound 3A
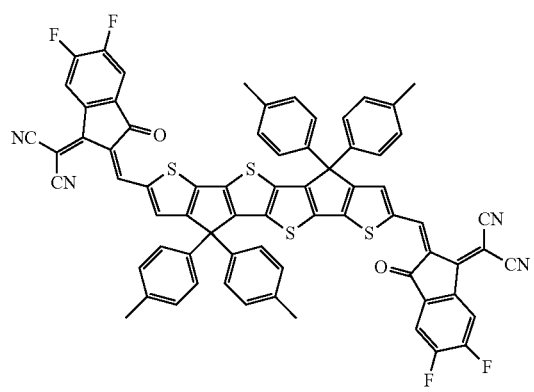
Model Comparative Compound 3B
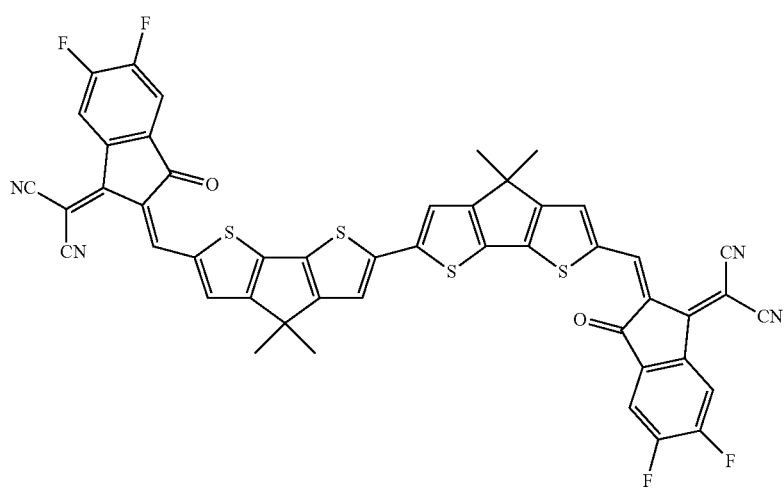

-continued

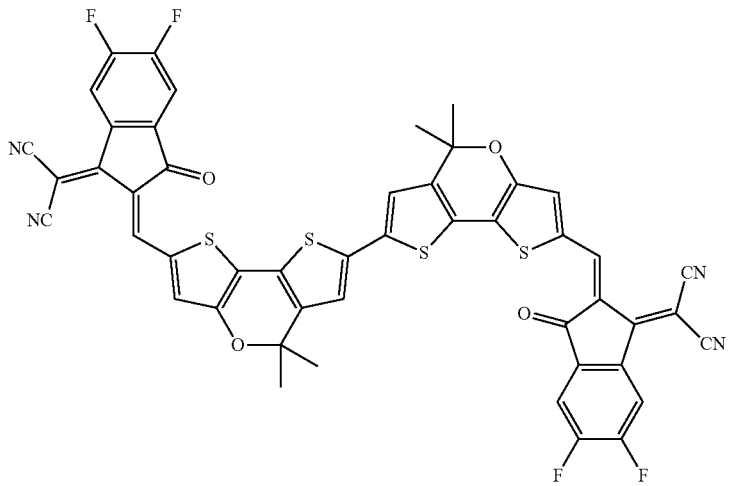

Model Compound Example 3

TABLE 3

| Compound | HOMO (eV) | LUMO (eV) | Band gap (eV) |
|---|---|---|---|
| Model Comparative Compound 1A | −5.147 | −3.409 | 1.738 |
| Model Comparative Compound 1B | −5.240 | −3.595 | 1.645 |
| Model Compound Example 1 | −5.215 | −3.610 | 1.605 |
| Model Comparative Compound 2A | −5.777 | −3.566 | 2.211 |
| Model Comparative Compound 2B | −6.092 | −3.901 | 2.191 |
| Model Compound Example 2 | −5.989 | −3.914 | 2.074 |
| Model Comparative Compound 3A | −4.954 | −3.411 | 1.543 |
| Model Comparative Compound 3B | −4.971 | −3.433 | 1.537 |
| Model Compound Example 3 | −4.952 | −3.468 | 1.484 |

The donor group EDG of Model Compound Example 1 has thiopenes bridging a central fused group and the acceptor (EAG) groups. This compound has a smaller band gap than Model Comparative Compounds 1A and 1B with a different central fused group, indicating that Model Compound Example 1 is capable of absorbing light at longer wavelengths than Model Comparative Compounds 1A and 1B.

A smaller band gap is also observed for Model Compound Example 2 as compared to Model Comparative Compounds 2A and 2B in which the bridging thiophene groups are not present.

Model Compound Example 3, in which n of formula (I) is 2, has a smaller band gap than either of Model Compound Examples 1 and 2, and a smaller band gap than either of Model Comparative Compounds 3A and 3B.

Figure 2:
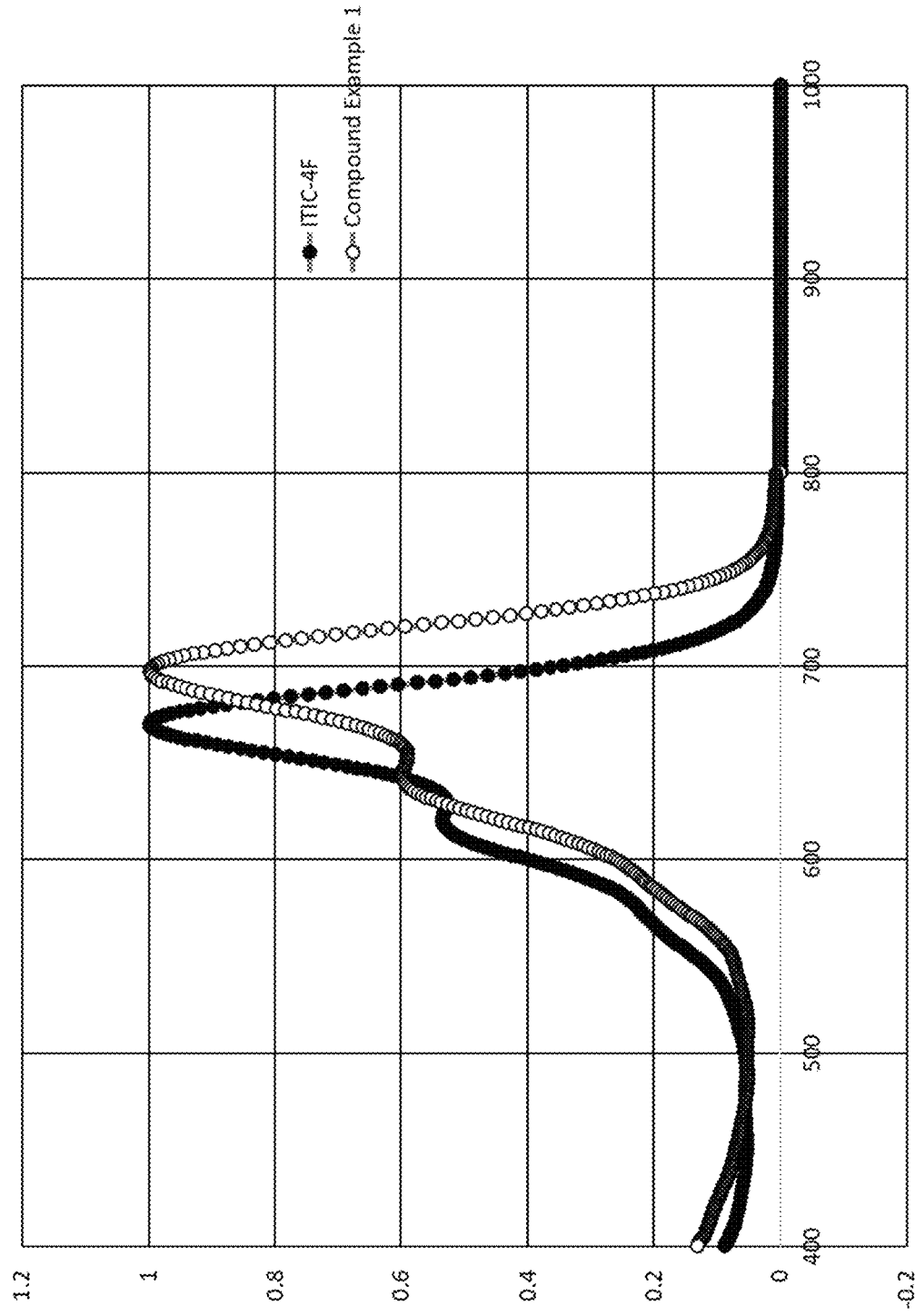
FIG. 2 shows absorption spectra for a material according to an embodiment of the present disclosure and a comparative material.

FIG. 2 shows absorption spectra for Compound Example 1 and ITIC-4F:

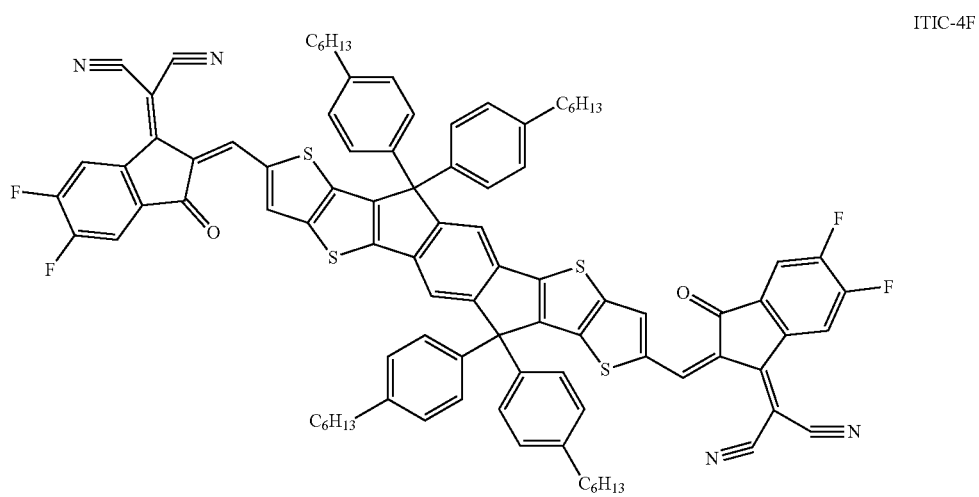

ITIC-4F

The invention claimed is:

1. A composition comprising an electron acceptor material and an electron donor material wherein the electron acceptor material is a compound of formula (I):

EAG-EDG-EAG    (I)

wherein each EAG is an electron-accepting group and EDG is a group of formula (II):

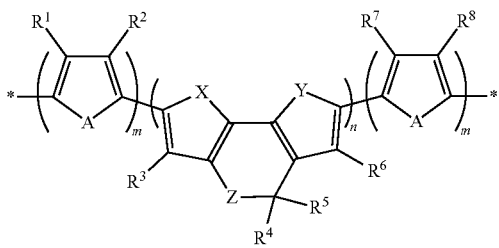

(II)

wherein:
n is at least 1;
each m is at least 1;
each X, Y and A is independently O, S or Se;
Z, independently in each occurrence if n is greater than 1, is O, S, C—O or NR$^9$ wherein R$^9$ is H or a substituent; and
R$^1$-R$^8$ are each independently selected from H or a substituent.

2. The composition according to claim 1 wherein each * is bound directly to an acyclic carbon-carbon double bond of EAG.

3. The composition according to claim 1 wherein each EAG is a group of formula (V):

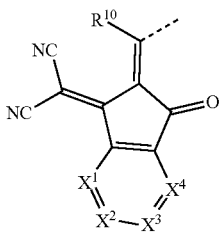

(V)

wherein:
R$^{10}$ in each occurrence is H or a substituent selected from the group consisting of: C$_{1-12}$ alkyl wherein one or more non-adjacent, non-terminal C atoms may be replaced with O, S, COO or CO and one or more H atoms of the alkyl may be replaced with F; and an aromatic group Ar$^2$ which is unsubstituted or substituted with one or more substituents selected from F and C$_{1-12}$ alkyl wherein one or more non-adjacent, non-terminal C atoms may be replaced with O, S, COO or CO;

---- represents a linking position to * of EDG; and
each X$^1$-X$^4$ is independently CR$^{12}$ or N wherein R$^{12}$ in each occurrence is H or a substituent selected from C$_{1-20}$ hydrocarbyl and an electron withdrawing group.

4. The composition according to claim 1 wherein each m is 1.

5. The composition according to claim 1 wherein X and Y are each S.

6. The composition according to claim 1 wherein Z is O or NR$^9$.

7. The composition according to claim 1 wherein the or each A is S.

8. The composition according to claim 1 wherein R$^1$-R$^8$ are each independent selected from the group consisting of:
H;
linear, branched or cyclic C$_{1-20}$ alkyl wherein one or more non-adjacent, non-terminal C atoms may be replaced by O, S, NR$^{12}$, CO or COO and wherein one or more H atoms of the C$_{1-20}$ alkyl may be replaced with F; and
a group of formula -(Ak)u-(Ar$^1$) v wherein Ak is a C$_{1-12}$ alkylene chain in which one or more C atoms may be replaced with O, S, CO or COO; u is 0 or 1; Ar$^1$ in each occurrence is independently an aromatic or heteroaromatic group which is unsubstituted or substituted with one or more substituents; and v is at least 1.

9. The composition according to claim 1 wherein n is at least 2.

10. A formulation comprising a composition according to claim 1 dissolved or dispersed in one or more solvents.

11. An organic photoresponsive device comprising an anode; a cathode; and a photosensitive organic layer disposed between the anode and cathode wherein the photosensitive organic layer comprises a composition according to claim 1.

12. An organic photoresponsive device according to claim 11 wherein the photoresponsive device is an organic photodetector.

13. A method of forming an organic photoresponsive device according to claim 11 comprising formation of the photosensitive organic layer over one of the anode and cathode and formation of the other of the anode and cathode over the photosensitive organic layer wherein formation of the photosensitive organic layer comprises deposition of a formulation comprising composition dissolved or dispersed in one or more solvents.

14. A photosensor comprising a light source and an organic photodetector according to claim 12 configured to detect light emitted from the light source.

15. A photosensor according to claim 14 wherein the light source emits light having a peak wavelength greater than 750 nm and/or wherein the organic photodetector is configured to detect light emitted from the light source following one or more of absorption, reflection and downconversion of light emitted from the light source.

16. A method of determining the presence and/or concentration of a target substance in a sample, the method comprising illuminating the sample and measuring a response of an organic photodetector according to claim 12.

* * * * *